(12) United States Patent
Pöhlmann et al.

(10) Patent No.: US 10,941,087 B2
(45) Date of Patent: Mar. 9, 2021

(54) PROCESS AND PLANT FOR THE ADIABATIC NITRATION OF AROMATIC COMPOUNDS

(71) Applicant: Josef Meissner GmbH & Co. KG, Köln (DE)

(72) Inventors: Jürgen Pöhlmann, Cologne (DE); Heinrich Hermann, Cologne (DE); Mirko Händel, Neunkirchen-Seelscheid (DE); Sophie Wernitz, Cologne (DE); Stefan Fankel, Königswinter (DE)

(73) Assignee: JOSEF MEISSNER GMBH & CO. KG

( * ) Notice: Subject to any disclaimer, the term of this patent is extended or adjusted under 35 U.S.C. 154(b) by 0 days.

(21) Appl. No.: 16/483,483

(22) PCT Filed: Dec. 14, 2017

(86) PCT No.: PCT/EP2017/082770
§ 371 (c)(1),
(2) Date: Aug. 5, 2019

(87) PCT Pub. No.: WO2018/141451
PCT Pub. Date: Aug. 9, 2018

(65) Prior Publication Data
US 2020/0017421 A1    Jan. 16, 2020

(30) Foreign Application Priority Data

Feb. 3, 2017 (DE) .......................... 102017000973.2
Mar. 30, 2017 (DE) .......................... 102017106881.3
May 10, 2017 (DE) .......................... 102017110084.9

(51) Int. Cl.
| | | |
|---|---|---|
| C07B 43/02 | (2006.01) | |
| B01D 11/04 | (2006.01) | |
| B01J 19/00 | (2006.01) | |
| B01J 19/24 | (2006.01) | |
| C07C 205/06 | (2006.01) | |

(52) U.S. Cl.
CPC .......... C07B 43/02 (2013.01); B01D 11/0488 (2013.01); B01J 19/0053 (2013.01); B01J 19/2415 (2013.01); B01J 19/2465 (2013.01); C07C 205/06 (2013.01)

(58) Field of Classification Search
CPC .... C07C 201/08; C07C 205/06; C07C 205/12
See application file for complete search history.

(56) References Cited

U.S. PATENT DOCUMENTS

2015/0175522 A1* 6/2015 Knauf .................. C07C 201/06
568/939

FOREIGN PATENT DOCUMENTS

| DE | 1468575 A1 | 6/1965 |
|---|---|---|
| DE | 1468575 | 2/1969 |
| EP | 0373966 | 6/1990 |
| EP | 0373966 A2 | 6/1990 |
| EP | 2877442 | 6/2015 |

(Continued)

*Primary Examiner* — Jafar F Parsa
(74) *Attorney, Agent, or Firm* — Edward E. Sowers; Brannon Sowers & Cracraft PC

(57) ABSTRACT

The invention relates to a method for preferably adiabatic nitration of nitratable aromatic organic compounds (aromatics) and to a corresponding plant, in particular a production plant (nitration plant) for carrying out said method.

14 Claims, 3 Drawing Sheets

(56) References Cited

FOREIGN PATENT DOCUMENTS

| | | | | |
|---|---|---|---|---|
| EP | 2877442 | A1 | 11/2016 | |
| GB | 995004 | * | 6/1965 | ........... C07C 205/06 |
| WO | 2014016292 | A1 | 1/2014 | |

* cited by examiner

000# PROCESS AND PLANT FOR THE ADIABATIC NITRATION OF AROMATIC COMPOUNDS

CROSS-REFERENCES TO RELATED APPLICATIONS

This application is a National Stage filing of International Application PCT/EP 2017/082770, filed Dec. 14, 2017, entitled PROCESS AND PLANT FOR THE ADIABATIC NITRATION OF AROMATIC COMPOUNDS, claiming priority to German Application Nos. DE 10 2017 000 973.2, filed Feb. 3, 2017, DE 10 2017 106 881.3, filed Mar. 30, 2017, and to DE 10 2017 110 084.9, filed May 10, 2017. The subject application claims priority to PCT/EP 2017/082770, to DE 10 2017 000 973.2, to DE 10 2017 106 881.3, and to DE 10 2017 110 084.9 and incorporates all by reference herein, in their entirety.

BACKGROUND OF THE INVENTION

The present invention relates to the technical field of nitration, in particular the preparation of nitrated organic aromatic compounds (hereinafter synonymously referred to as "nitroaromatics", "nitration products", "aromatic nitro products", "aromatic nitro compounds", "nitrated products" or the like), preferably by adiabatic nitration.

In particular, the present invention relates to a process for the nitration, in particular adiabatic nitration, of nitratable aromatic organic compounds (aromatics) to give the corresponding nitrated aromatic organic compounds (nitroaromatics).

The present invention further relates to a production plant (nitration plant or plant) for the nitration, in particular adiabatic nitration, of nitratable aromatic organic compounds (aromatics) to give nitrated products in the form of the corresponding nitrated aromatic organic compounds (nitroaromatics), in particular a production plant for carrying out the process of the invention.

Finally, the present invention relates to the use according to the invention of nitrated aromatic organic compounds (nitroaromatics).

Aromatic nitro compounds (e.g. nitrobenzene (MNB), mononitrotoluene (MNT), dinitrotoluene (DNT), trinitrotoluene (TNT), nitrochlorobenzene (MNCB), etc.) are usually prepared by nitration of corresponding starting aromatics (e.g. benzene, toluene, xylene, chlorobenzene, dichlorobenzenes, etc.), in particular by reaction of the corresponding starting aromatics with nitric acid in the presence of sulfuric acid as catalyst and water-binding agent, i.e. by reaction of the corresponding starting aromatics with a nitrating acid (i.e. a nitric acid/sulfuric acid nitrating acid mixture, which at the beginning of the reaction is also referred to as mixed acid and at the end of the reaction is also referred to as spent (nitrating) acid).

In the prior art, the nitration of aromatics by means of the nitric acid/sulfuric acid nitrating acid mixture is preferably carried out as heterogeneous liquid/liquid mixture of organic phase and acid phase, with the reaction of the aromatics to be nitrated with the nitric acid to form the corresponding nitroaromatics taking place in the acid phase. To that end, the aromatic to be nitrated therefore firstly has to be transferred from the organic phase into the acid phase in order to be able to react therewith. The nitroaromatic formed in the acid phase then separates out, after the solubility limit has been exceeded, as organic phase; this organic phase consists predominantly of the aromatic to be nitrated at the beginning of the nitration and mainly of the desired nitroaromatic at the end of the reaction, when either the entire nitric acid or aromatic to be nitrated has been reacted.

A prerequisite for rapid and effective reaction of the aromatic is that sufficient aromatic to be nitrated is always transferred from the organic phase into the acid phase. This is typically achieved by generation of a very large exchange area between the two abovementioned phases, especially either by dispersing the organic phase in the acid phase (oil-in-water or O/W emulsion) or, conversely, the acid phase in the organic phase (water-in-oil or W/O emulsion). The greater the exchange area between organic phase and acid phase (i.e. the smaller the droplet size of the disperse phase), the greater is the conversion in the nitration, e.g. in the nitration of benzene to give nitrobenzene or of toluene to give mononitrotoluene, etc. (as in all mass transfer-limited reactions).

When, for example, the nitration is carried out continuously and isothermally in stirred vessels or in cocurrent and/or countercurrent in cascades of stirred vessels constant conditions, e.g. composition of the organic phase and of the acid phase and, associated therewith, constant physicochemical conditions or parameters for the two-phase mixture of organic phase and acid phase prevail in each reactor. The nitration proceeds under always the same conditions in each reactor.

On the other hand, a nitration in a stirred vessel in batch operation with complete backmixing or in a tube reactor with plug flow without backmixing proceeds quite differently. In both cases, not only the composition of the organic phase and of the acid phase but also their physicochemical conditions or parameters, in particular density, interfacial tension, etc., change continually as the nitration progresses. Under continually changing conditions or parameters, it is much more difficult or virtually impossible to produce a constant exchange area for a controlled reaction over the entire time of the reaction.

It is also known that pure aromatics such as benzene or toluene can be dispersed only with difficulty in sulfuric acid or nitrating acid mixtures and that dispersions of aromatics in sulfuric acid or nitrating acid mixtures coalescence coalesce relatively quickly. As described, for example, in EP 0 373 966 A2, a conversion of nitric acid of only 55.3% and of benzene of only 52.5% are achieved in the case of one-off dispersion of the aromatic to be nitrated (benzene) in a mixed acid because of excessively rapid coalescence of the organic phase. It is therefore necessary in the case of a nitration in which two phases are present in the nitration mixture (namely firstly an organic phase composed of aromatic to be nitrated and nitroaromatic produced and secondly nitrating acid mixture) for mixing energy to be introduced continually so that the required exchange area between the two phases is maintained and the desired conversion is thus achieved at a given residence time.

Especially at the beginning of a nitration (e.g. in a tube reactor), a particularly large quantity of mixing energy has to be supplied in order to produce and maintain a sufficiently large exchange area between organic phase and acid phase, so that the nitration is initiated or starts and also progresses. If this does not occur, a dramatic decrease in the exchange area occurs as a result of more or less rapid coalescence of the disperse phase, associated with a drastic decrease in the conversion of the aromatic to be nitrated per unit time.

If, for example, it is not always ensured in a tube reactor over the entire length of the reactor (as described, for example, in EP 1 272 268 A2, EP 1 291 078 A2 or EP 0 708 076 A2) that the incipient coalescence of the organic phase dispersed in the nitrating acid is prevented by supply of additional mixing energy by renewed introduction of mixing energy into an initially produced dispersion of the aromatic to be nitrated (e.g. benzene) in the nitrating acid mixture, the nitration breaks down, which can be recognized from no heat of nitration being liberated anymore even though nitric acid is still present in the nitrating acid and aromatic to be nitrated is still present in the organic phase.

A corresponding situation applies at the beginning of the reaction: if the droplet size produced at the beginning of the reaction is not small enough and the exchange area is thus too small, the mass transfer-limited reaction of benzene or toluene, for example, to form nitrobenzene or mononitrotoluene proceeds only slowly, which can be recognized by no or only a small temperature rise being observed in the reaction mixture because the reaction does not start. Conversely, when the droplet size of the disperse phase is sufficiently small and the exchange area is thus large, rapid reaction of the aromatic to be nitrated occurs under otherwise identical conditions, which can be recognized by a rapid temperature rise being observed in the reaction mixture and, associated therewith, a desired high conversion of aromatic to be nitrated into the corresponding nitroaromatic being observed.

Especially in adiabatic reactions (e.g. in the adiabatic nitration of benzene to give nitrobenzene), the conversion and the time required for this depends not only on the exchange area between the two phases and thus the droplet size of the disperse phase but also on further generally known parameters such as the concentration of sulfuric acid and nitric acid in the nitrating acid (referred to as mixed acid at the beginning of the reaction and as spent acid at the end), the initial temperature (cf. for example, EP 2 168 942 A1), the phase ratio between organic phase and acid phase and, associated therewith, the final temperature, etc.

The conversion in an adiabatic nitration (e.g. of benzene to give nitrobenzene) in a tube reactor is, proceeding from a defined initial temperature, characterized by the increase in the temperature of the nitration mixture as a result of the heat of nitration liberated (cf., for example, EP 2 168 942 A1 and EP 1 272 268 A2). The temperature difference determined for a particular nitration mixture (also referred to as delta T or $\Delta T$) can be correlated directly, in particular linearly, with the conversion of nitric acid, as described, for example, in EP 2 168 942 A1.

In order to achieve the greatest possible conversion at a prescribed residence time in a tube reactor (e.g. more than 98% of the nitric acid introduced), it is necessary for there to be not only optimal dispersion of the aromatic to be nitrated in the mixed acid but also a suitable initial temperature for the reaction to be initiated or to start, i.e. so that after mixing of the starting materials a reaction occurs in such a way that a steep, in particular uniform, preferably exponential temperature increase in the nitration mixture is observed and, for example, at least 60% of the nitric acid introduced is reacted in the first 13% by volume of the reaction space of a tube reactor (cf., for example, EP 2 168 942 A1). This is achieved, for example, by a specific arrangement of the dispersing elements for the required redispersion of the organic phase which at the beginning coalesces quickly in the tube reactor (cf., for example, EP 1 272 269 A1).

The initial temperature can, for example, be selected in the range from 50 to 120° C. The mixing of various heated feed streams (i.e. sulfuric acid, nitric acid and aromatic to be nitrated, e.g. benzene, cf. for example, EP 0 436 443 A2 or EP 1 272 269 A1) results in a mixing temperature, with the main contribution to the initial temperature coming from the sulfuric acid which is present in a large excess.

At a given residence time, the initial temperature controls not only the conversion but also the formation of the by-products typical of an adiabatic nitration, for example of benzene to give nitrobenzene, in particular the amount of dinitrophenols and trinitrophenols (picric acid) and of dinitrobenzene (DNB).

At initial temperatures of from 80 to 120° C. (cf., for example, U.S. Pat. No. 4,091,042 A), preferably greater than 97° C. and particularly preferably from 100 to 120° C. (cf., for example, EP 0 436 443 A2 or EP 2 168 942 A1), it is possible to achieve conversions of nitric acid of at least 99% at residence times in the reaction tube of less than 2 minutes (e.g. not more than 25 seconds, cf., for example, EP 0 436 443 A2).

At lower initial temperatures, on the other hand, significantly longer residence times are required. At an initial temperature of, for example, about 80° C., a residence time of 300 seconds has been described as necessary in order to achieve complete conversion of the nitric acid in plants according to the prior art (tube reactor) (cf., for example, U.S. Pat. No. 8,692,035 B2 or WO 2010/051616 A1).

Compared to plants according to the prior art, in which initial temperatures of from about 97 to 110° C. are employed, significantly larger nitration reactors are therefore required for lower initial temperatures, but these are significantly more expensive since they are usually made of enameled steel.

As a plant output of, for example, 20 metric tons of nitrobenzene (NB) per hour (i.e. 20 t of NB/h), a tube reactor having a diameter of 250 mm operating at a flow velocity of the nitration mixture of 1.25 m/s and a residence time of at least 300 s would be a factor of 2.5 longer (i.e. about 375 m) than a standard reactor according to the prior art having a length of 150 m and operated at a residence time of 120 s under otherwise identical conditions (i.e. same mixed acid composition, same phase ratio, etc.).

A further objective of optimization of plants for the adiabatic nitration of aromatics, in particular benzene, is to minimize the amount of by-products in the nitrobenzene. As has already been described in EP 0 436 443 A2, the formation of dinitrophenols and trinitrophenols increases rapidly with increasing final temperature of the nitration mixture. For these reasons, too, the final temperature in the nitration mixture should not exceed 135 to 145° C. The content of nitrophenols in the crude nitrobenzene (crude NB) is then in the range from 2000 to 3000 ppm. The content of dinitrobenzene (DNB) at these final temperatures is in the range from 200 to 250 ppm. The removal of these nitrophenols from the crude nitrobenzene and destruction of these in the wastewater, for example by means of a thermolysis (as described in EP 0 953 546 A2 and EP 0 005 203 A2), is complicated and expensive.

The formation of by-products can be greatly reduced by lowering the initial temperature and thus also the final temperature. Each decrease in the initial temperature by 20 to 25° C. leads to a halving of the nitrophenol content in the crude nitrobenzene. Lowering of the initial temperature from about 110° C. to about 80° C. leads to a reduction in the nitrophenol content by about 50%, i.e. to about 1500 ppm and less (e.g. 1000 ppm), compared to the circumstances described, for example, in EP 0 436 443 A2, particularly preferably to a value of about 1000 ppm. The content of dinitrobenzene (DNB) decreases analogously to about 100 ppm (cf., for example, U.S. Pat. No. 8,692,035 B2 or WO 2010/051616 A1).

The temperature rise in the nitration mixture between initial temperature and final temperature can be controlled, at a given nitric acid concentration in the mixed acid, by the phase ratio between acid phase and organic phase. At a constant phase ratio and the same sulfuric acid concentration and initial temperature in the starting mixed acid, the final temperature of the nitration mixture increases with increasing content of nitric acid in the mixed acid and at the same conversion, and vice versa.

As has already been described in EP 0 771 783 A1, it is advantageous for a high initial conversion to be achieved at the beginning of the reaction in the tube reactor by optimal mixing of the phases in order to obtain a high selectivity. The prior art describes various measures aimed at achieving very optimal dispersion of the aromatic to be nitrated in the starting mixed acid at the beginning of the reaction and achieving redispersion (cf., for example, EP 0 373 966 A2, EP 0 489 211 A1, EP 0 771 783 A1, EP 0 779 270 A1, EP 1 272 269 A1, EP 1 291 078 A2 and EP 2 168 942 A1).

Optimal dispersion of the aromatic to be nitrated (e.g. benzene) in the nitrating acid, especially at the beginning of the nitration in order to start the reaction, is a prerequisite for a high conversion (cf. EP 1 272 269 A1 or EP 2 168 942 A1). As stated in this respect in U.S. Pat. No. 9,284,256 B2 and EP 2 877 442 A1, the addition of more than 4% of aliphatic hydrocarbons to the benzene to be nitrated can lead to the nitration not starting, i.e. to no appreciable temperature rise in the nitration mixture being observed after combining the starting materials and initial dispersing, while under otherwise identical conditions using a benzene having a content of less than 0.1% of aliphatics the nitration starts (as described in EP 1 272 269 A1 or EP 2 168 942 A1) with a steep temperature rise in the first 13% by volume of the tube reactor and proceeds as intended.

There have been many attempts in the prior art to achieve improved dispersing of the aromatic to be nitrated in the nitrating acid. One measure known from the prior art for achieving this is, for example, a large ratio of acid phase to organic phase, by means of which the dispersibility of the organic phase is said to be improved and the coalescence is said to be reduced, as described, for example, in EP 0 436 443 A2 and U.S. Pat. No. 8,692,035 B2. A further measure known from the prior art, as set forth in EP 1 272 268 A2 and EP 2 168 942 A1, is to carry out the nitration in a tube reactor having mixing and dispersing elements and to achieve a uniform, in particular exponential, preferably S-shaped temperature increase at the beginning of the reaction and a very high conversion in the front section of the tube reactor by means of nonuniform arrangement or distribution of the mixing and dispersing elements over the total length of the tube reactor. However, the measures known from the prior art are not sufficient in order to always achieve optimal dispersion of the aromatic to be nitrated in the nitrating acid and compensate for the problems and disadvantages associated with an unsatisfactory dispersion and indicated above.

BRIEF SUMMARY OF THE INVENTION

It is therefore an object of the present invention to provide a process and a corresponding production plant, i.e. production plant suitable for carrying out this process (nitration plant or plant), for the nitration, in particular adiabatic nitration, of nitratable aromatic organic compounds (aromatics), with the abovementioned disadvantages and inadequacies of the prior art being at least largely avoided or at least decreased.

In particular, it is an object of the present invention to provide a process and a corresponding production plant suitable for carrying out this process (nitration plant or plant) for the nitration, in particular adiabatic nitration, of nitratable aromatic organic compounds (aromatics) by means of which the nitratable aromatic organic compounds can be converted or reacted in a technically efficient and safe and simple way to give the corresponding nitrated aromatic organic compounds (nitroaromatics).

A further object of the present invention is to provide a process and a corresponding production plant suitable for carrying out this process (nitration plant or plant) for the nitration, in particular adiabatic nitration, of nitratable aromatic organic compounds (aromatics), with, in the context of the nitration, the dispersing of the aromatics to be nitrated in the nitrating acid mixture being improved, especially at the beginning of the reaction, preferably immediately after combining of the starting materials. In particular, the dispersing of organic phase and acid phase should, even under unfavorable conditions (e.g. in the presence of impurities such as an increased content of aliphatics in the aromatic to be nitrated, at an initial temperature which is too low or in the case of a low input of dispersing energy), be improved in such a way that the nitration can still be carried out efficiently, in particular the nitration mixture can be converted to an extent of at least 98% at the prescribed reaction or residence time in the reactor.

Finally, it is also an object of the present invention to provide a process and a corresponding production plant suitable for carrying out this process (nitration plant or plant) for the nitration, in particular adiabatic nitration, of nitratable aromatic organic compounds (aromatics), in which, in the context of the nitration, improved dispersion can be achieved immediately after contacting (e.g. mixing) of the reactants, in particular of nitrating acid phase containing nitric acid and organic phase containing the aromatics to be nitrated, preferably with avoidance of rapid coalescence of the aromatics to be nitrated in the nitrating acid, preferably with the objective of starting the nitration reaction even at relatively low initial temperatures compared to the prior art (and without longer reaction or residence times being required compared to processes according to the prior art with higher initial temperatures but otherwise the same conditions).

According to the invention, the objects indicated above are achieved, according to a first aspect of the invention, by a process; according to a second aspect of the invention, a production plant (nitration plant or plant); and finally, according to a third aspect of the invention, the use according to the invention.

It goes without saying that variants, embodiments, advantages or the like which are set forth below for only one aspect of the invention of course also apply, in order to avoid unnecessary repetition, analogously in respect of all other aspects of the invention.

Furthermore, it goes without saying that when values, figures and ranges are indicated below, the respective values, figures and ranges indicated are not to be interpreted as restrictions; it will be obvious to a person skilled in the art that it is possible to deviate from the specified ranges or figures for individual cases or applications without going outside the scope of the present invention.

In addition, all values or parameters or the like indicated below can in principle be measured or determined using standardized or explicitly mentioned methods of determination or else using methods of determination or analysis with which a person skilled in this field will be familiar per se.

This having been said, the present invention will be described in more detail below.

DETAILED DESCRIPTION OF THE INVENTION

Figure 1:
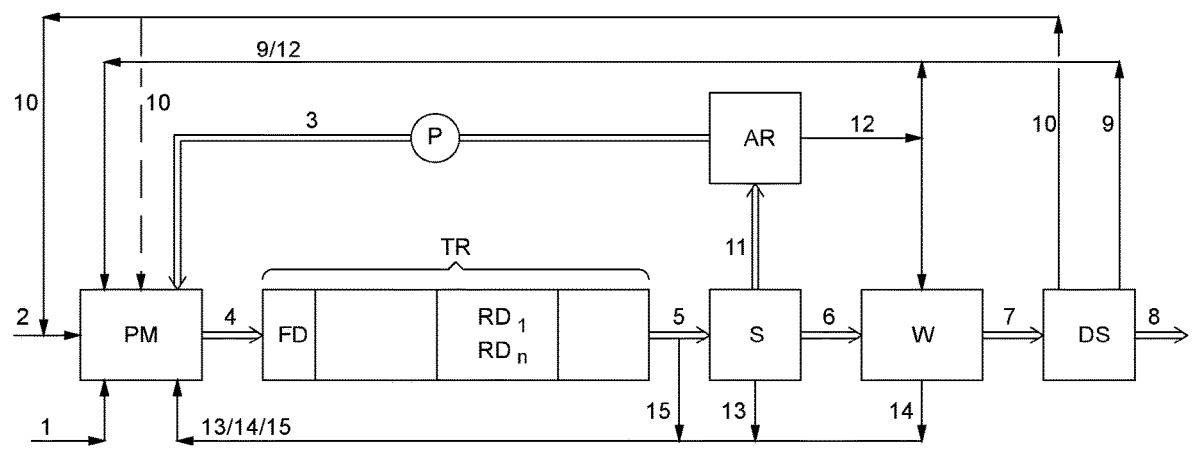
FIG. 1 a schematic depiction of a process according to the invention or a production plant according to the invention as per a preferred embodiment of the present invention.

The present invention thus provides, according to a first aspect of the present invention, a process for the nitration, in particular adiabatic nitration, of nitratable aromatic organic compounds (aromatics) to give the corresponding nitrated aromatic organic compounds (nitroaromatics),
wherein nitratable aromatic organic compounds (aromatics) are converted in a nitration reaction with a nitric acid/sulfuric acid nitrating acid mixture (i.e. "mixed acid") into the corresponding nitrated aromatic organic compounds (nitroaromatics),
where the process of the invention is characterized
in that corresponding nitrated aromatic organic compounds (nitroaromatics) are added to the starting reaction mixture which comprises the nitratable aromatic organic compounds (aromatics) and the nitric acid/sulfuric acid nitrating acid mixture and the conversion and/or nitration reaction is started and/or carried out in the presence of the nitrated aromatic organic compounds (nitroaromatics); and/or
in that the nitrated aromatic organic compounds (nitroaromatics) obtained are partly recirculated to the nitration reaction and the subsequent conversion and/or nitration reaction is started and/or carried out in the presence of the nitrated aromatic organic compounds (nitroaromatics).

The term corresponding nitrated aromatic organic compounds (nitroaromatics), as is used according to the invention, refers, in the context of the present invention, especially to those nitroaromatics which can be prepared by nitration, preferably mononitration, of the starting aromatics used. Thus, for example, mononitrobenzene (MNB) is the corresponding nitrated aromatic organic compound (nitroaromatic) to benzene, mononitrotoluene (MNT) is that to toluene, mononitrochlorobenzene is that to chlorobenzene, etc.

The process of the invention, like the (production) plant according to the invention described in detail below for carrying out the process of the invention, is associated with numerous special aspects and advantages which will be discussed in detail below:

The applicant has surprisingly found, in the context of the present invention, that the addition of nitrated product to the starting reaction mixture leads to a lowering of the interfacial tension between organic phase and acidic aqueous phase or acid phase (where the organic phase comprises the starting aromatics to be nitrated and the added nitrated products and optionally nitration by-products and where the acidic aqueous phase or the acid phase in the starting reaction mixture at the beginning of the reaction comprises sulfuric acid and after addition of the nitric acid the nitrating acid or mixed acid and at the end of the reaction comprises the aqueous spent nitrating acid or the aqueous spent nitrating acid mixture and optionally proportions of added nitroaromatic and/or nitroaromatic formed in the nitration dissolved therein). In this way, significantly improved dispersibility or emulsifiability between organic phase and aqueous acidic phase or acid phase is achieved, i.e. the nitrated end product or the nitrated aromatic thus functions as dispersant (disperser) or emulsifier in the starting reaction mixture. It is, so to say, a dispersant or emulsifier intrinsic or inherent to the system since no substances which are extraneous to the reaction and could contaminate the reaction products are used.

Overall, improved, in particular intimate mixing and dispersion of the two phases (i.e. organic phase and acid phase) is achieved by addition of nitrated product to the starting reaction mixture, so that overall improved and more rapid exchange between the two phases takes place. As a result, a more rapid conversion or more rapid nitration reaction also occurs, in particular with improved yields, in particular improved space-time yields.

In addition, a significantly smaller amount of by-products is formed in the reaction procedure according to the invention. Overall, the reaction or process procedure and the nitration reaction can be controlled better by addition of nitrated product to the starting reaction mixture.

Apart from the shortened reaction times and the more rapid reactions with improved yields and lower by-product formation, the initial temperature for starting-up and initiating the reaction can, in the process of the invention, also be significantly decreased compared to conventional nitration processes having otherwise identical conditions, i.e. significantly lower (reaction) starting temperatures for the nitration reaction can be used in the process of the invention, as will be discussed in more detail below.

In summary, the present invention therefore provides an improved, in particular adiabatic, nitration process for nitratable aromatic organic compounds which displays an overall improved efficiency, in particular an improved technical efficiency and an improved energy efficiency, and overall improved process economics and in addition improved handleability.

In the context of the present invention, it is possible, particularly in the case of an adiabatic reaction procedure for the nitration (e.g. adiabatic nitration of benzene to give mononitrobenzene in a tube reactor), to improve the dispersing of the aromatic to be nitrated in the nitrating acid mixture, in particular at the very beginning of the reaction, preferably immediately after contacting (e.g. mixing) of the starting materials, in such a way that even under unfavorable conditions (e.g. in the presence of impurities such as an increased content of aliphatics in the aromatic to be nitrated or in the case of an initial temperature which is too low or in the case of a low input of dispersing energy) the nitration can still be carried out efficiently, in particular so that the nitration mixture can be reacted to an extent of at least 98%, in particular at least 99%, preferably at least 99.5%, in each case based on the nitric acid conversion in the nitrating acid mixture, in the prescribed reaction or residence time in the reactor.

The process of the invention makes it possible, in the context of the nitration, to achieve improved dispersion immediately after contacting (e.g. mixing) of the reactants, in particular of nitrating acid phase containing nitric acid and organic phase containing the aromatics to be nitrated, preferably with avoidance of rapid coalescence of the aromatics to be nitrated in the nitrating acid, preferably with the objective of starting the nitration reaction even at relatively low initial temperatures compared to the prior art (and without longer reaction or residence times than in processes according to the prior art using higher initial temperatures but otherwise the same conditions being required). In particular, the process of the invention allows, even at (reaction) start temperatures below 100° C., preferably below 95° C., particularly preferably below 90° C., the nitration to be initiated or started in such a way that there is no need for longer reaction or residence times than in processes according to the prior art with higher initial temperatures but otherwise the same conditions.

The present invention thus makes it possible for nitratable aromatic organic compounds (i.e. aromatics) to be converted or reacted in a technically efficient and safe and simple way to give the corresponding nitrated aromatic organic compounds (nitroaromatics).

In the context of the present invention, it was thus found, completely surprisingly, that addition of nitrated product (e.g. nitrobenzene in the case of the nitration of benzene) to the starting reaction mixture results in significantly improved initial dispersion of the aromatic to be nitrated (in particular characterized by a steeper temperature rise in the nitration mixture after initial dispersing which triggers the nitration) and also a reduced tendency for this dispersion to coalesce being observed.

In other words, the invention thus provides, in particular, an overall improved, preferably adiabatic process for obtaining nitroaromatics (e.g. nitrobenzene, nitrotoluene, nitrochlorobenzene, etc.) by means of a preferably adiabatic reaction of the corresponding starting aromatics (e.g. benzene, toluene, chlorobenzene, etc.) with nitric acid in the presence of sulfuric acid as water-binding agent and catalyst, preferably in a tube reactor and preferably using a stoichiometric excess of aromatic to be nitrated, with a proportion of the corresponding nitroaromatic (e.g. nitrobenzene in the case of the nitration of benzene) being added to or mixed into the reaction batch or the starting reaction mixture.

As indicated in detail below, the process of the invention can be carried out completely flexibly: thus, the proportion of nitroaromatic to be added or mixed in (e.g. nitrobenzene in the case of the nitration of benzene) can, for example, be added to the recycled or fresh sulfuric acid required for the nitration and/or to the aromatic to be nitrated before the first joint dispersing of the further starting materials (i.e. sulfuric acid and nitric acid) and/or to only part of the aromatic to be nitrated before the first joint dispersing of the further starting materials (i.e. sulfuric acid and nitric acid and also remaining part of the aromatic to be nitrated), etc., with combinations of these variants also being possible. In principle, the only important thing is that sufficient amounts of nitroaromatic are present in the starting reaction mixture at the beginning of the nitration reaction to ensure efficient dispersion of organic phase and acid phase.

Particular, advantageous or preferred embodiments of the process of the invention will be described below:

As described above, the conversion and/or nitration reaction is preferably carried out under adiabatic reaction conditions in the process of the invention.

In a particular embodiment of the present invention, the conversion and/or nitration reaction is also carried out, in particular, as mononitration.

In a further particular embodiment of the present invention, the process is usually carried out in such a way that the starting reaction mixture and the nitrated aromatic organic compounds (nitroaromatics) are present as liquid/liquid mixture of organic phase and acid phase, in particular acidic aqueous phase, under the selected reaction conditions. In particular, the organic phase can comprise nitratable aromatic organic compounds (aromatics) and nitrated aromatic organic compounds (nitroaromatics) and/or, in particular, the acid phase (i.e. in particular the acidic aqueous phase) can comprise nitric acid, sulfuric acid and optionally water (and optionally proportions of added nitroaromatic and/or nitroaromatic formed in the nitration dissolved therein).

In the process of the invention, the nitratable aromatic organic compounds (aromatics) and the nitric acid/sulfuric acid nitrating acid mixture and the (added or recirculated) nitrated aromatic organic compounds (nitroaromatics) form the (starting) nitration mixture (i.e. the initial nitration mixture or the nitration mixture present at the beginning of the conversion and/or nitration reaction); in other words, the nitration mixture (i.e. the initial nitration mixture or the nitration mixture present at the beginning of the conversion and/or nitration reaction) comprises the starting reaction mixture which comprises the nitratable aromatic organic compounds (aromatics) and the nitric acid/sulfuric acid nitrating acid mixture and also the nitrated aromatic organic compounds (nitroaromatics). In contrast, the nitration mixture obtained or resulting after conversion and/or at the end of the nitration reaction comprises at least substantially spent nitrating acid and nitrated aromatic organic compounds (nitroaromatics) and optionally small amounts of unreacted nitratable aromatic organic compounds (aromatics) (together with any impurities and by-products present).

In principle, virtually any nitratable aromatic organic compounds (aromatics) can be nitrated according to the present invention.

In a particular embodiment of the present invention, the nitratable aromatic organic compounds (aromatics) can be liquid under the selected reaction conditions. In particular, the nitratable aromatic organic compounds (aromatics) can be present in the liquid state under standard pressure (1.01325 bar) and at a temperature of 70° C. or above, in particular 50° C. or above, preferably 25° C. or above, particularly preferably 10° C. or above. This makes an efficient reaction procedure possible.

In particular, the nitratable aromatic organic compounds (aromatics) can be selected from among optionally halogenated monocyclic or polycyclic organic aromatics.

In a particular embodiment of the present invention, the nitratable aromatic organic compounds (aromatics) used for the nitration can, in particular, be selected from the group consisting of benzene, mononitrobenzene (MNB), halogenated benzenes, in particular monochlorobenzene and dichlorobenzenes, mononitrated halogenated benzenes, toluene, mononitrotoluene (MNT), dinitrotoluenes (DNT) and xylenes, and also mixtures and combinations thereof. Particular preference is given to benzene.

In principle, virtually any nitrated aromatic organic compounds (nitroaromatics) can be prepared according to the present invention.

As regards the nitrated aromatic organic compounds (nitroaromatics) prepared, these can, in particular, be liquid under the selected reaction conditions. In particular, the nitrated aromatic organic compounds (nitroaromatics) can be present in the liquid state under standard pressure (1.01325 bar) and at a temperature of 70° C. or above, in particular 50° C. or above, preferably 25° C. or above, particularly preferably 10° C. or above. This ensures that the process proceeds efficiently.

The nitrated aromatic organic compounds (nitroaromatics) prepared can, in particular, be selected from among optionally halogenated monocyclic or polycyclic mononitrated, dinitrated or trinitrated organic aromatics.

In a particular embodiment of the present invention, the nitrated aromatic organic compounds (nitroaromatics) prepared can be selected from the group consisting of mononitrobenzene (MNB), dinitrobenzenes (DNB), halogenated mononitrobenzenes and dinitrobenzenes, in particular mononitrated and dinitrated monochlorobenzenes and dichlorobenzenes, mononitrotoluenes (MNT), dinitrotoluenes (DNT), trinitrotoluene and mononitrated and dinitrated xylenes and also mixtures and combinations thereof. Particular preference is given to mononitrobenzene.

In a preferred embodiment of the present invention, benzene is used as nitratable aromatic organic compound (aromatic) and mononitrobenzene (MNB) is obtained as nitrated aromatic organic compound (nitroaromatic).

In a common embodiment of the process of the invention, the conversion and/or nitration reaction can be followed by a removal of the acidic aqueous phase (acid phase) and/or a phase separation of the nitration mixture obtained into spent nitrating acid and crude nitrated aromatic organic compounds (crude nitroaromatics), preferably followed by scrubbing of the crude nitrated aromatic organic compounds (crude nitroaromatics) with a scrubbing medium, in particular in one or more scrubbing steps, preferably with subsequent removal of the used scrubbing medium to give the scrubbed nitrated aromatic organic compounds (nitroaromatics) which have been freed of impurities, (i.e. purified) in this way.

In a preferred embodiment of the present invention, the scrub can be carried out in at least two scrubbing steps, with at least one acidic scrubbing step ("acid scrub") and at least one neutral scrubbing step ("neutral scrub") being able to be provided.

The scrub can preferably comprise (i) at least one first scrubbing step carried out in an acidic medium ("acid scrub"), preferably using water or a mineral acid as scrubbing medium, (ii) at least one second scrubbing step carried out in an alkaline (basic) medium ("basic scrub"), preferably using a base as scrubbing medium, and (iii) at least one third scrubbing step carried out in a neutral medium ("neutral scrub"), preferably using water as scrubbing medium (and in the abovementioned order or sequence from first to third scrub).

In a particular embodiment of the present invention, the used scrubbing medium can be recycled and/or circulated and/or recirculated to the scrub, in particular after purification.

As indicated above, the scrub of the crude nitroaromatics in order to remove the acids of the nitration mixture, the nitrophenols and other acidic impurities and other impurities which can be extracted by means of the scrubbing medium, which are dissolved and suspended therein, usually comprises three scrubbing steps (see, for example, F. Meissner et al., Industrial and Engineering Chemistry, vol. 46, pages 718 to 724 (1954); Ullmanns Enzyklopädie der Technischen Chemie, 4$^{th}$ edition, vol. 17, pages 384 to 386; H. Hermann et al., "Industrial Nitration of Toluene to Dinitrotoluene", ACS Symposium Series 623 (1996), pages 234 to 249, Editors: L. F. Albright, R. V. C. Carr, R. J. Schmitt; U.S. Pat. No. 6,288,289 B1; EP 1 816 117 B1). As scrubbing medium, it is usually possible to use water, with the scrub usually being carried out as liquid/liquid scrub (i.e. at temperatures at which the nitroaromatic to be scrubbed is present as liquid). Furthermore, the vapor condensate from the reconcentration of the spent nitrating acid can, according to the present invention, also be used as scrubbing medium in the acid scrub (scrubbing step (i)) or in the alkaline scrub (scrubbing step (ii)).

As indicated above, the three-step scrub usually comprises the following steps:
(i) an acid scrub using water in order to remove the dissolved and suspended mineral acids, e.g. sulfuric acid, nitric acid and oxides of nitrogen ("acid scrub");
(ii) a basic or alkaline scrub in the presence of a base ("alkaline scrub"), e.g. sodium carbonate (soda), sodium bicarbonate, sodium sulfite, sodium hydrogensulfite, ammonia, sodium hydroxide, potassium hydroxide, etc. (see, for example, U.S. Pat. No. 4,482,769 A, 4,597,875 A or 6,288,289 B1), in order to remove the weakly acidic impurities dissolved in the crude nitroaromatic, e.g. the nitrophenols, nitrocresols, nitrobenzoic acids, degradation products from the oxidative decomposition of the phenols or of aliphatic or cyclic hydrocarbons, etc., e.g. oxalic acid, etc., or the asymmetric isomers in the case of TNT ("basic scrub");
(iii) a neutral scrub in order to remove residue traces of alkali and to further reduce the impurities still remaining in traces in the product ("neutral scrub").

The objective of these scrubbing steps is, in particular, to obtain not only a pure product but also very little wastewater per metric ton of product, in which wastewater the scrubbed-out impurities are present in such a form that they can be disposed of inexpensively.

A particular embodiment of the present invention advantageously provides for the spent nitrating acid obtained after the conversion and/or nitration reaction to be, after the crude nitrated aromatic organic compounds (crude nitroaromatics) have been separated off, recycled and/or circulated and/or recirculated to the nitration reaction, in particular after concentration and/or after addition of fresh nitric acid and/or sulfuric acid. The process efficiency is increased further in this way.

Furthermore, the amount of nitrated aromatic organic compounds (nitroaromatics) added and/or recirculated for the conversion and/or nitration reaction can also vary within a wide range.

In a particular embodiment of the present invention, the amount of nitrated aromatic organic compounds (nitroaromatics) added and/or recirculated for the conversion and/or nitration reaction can advantageously be selected in such a way that the amount of added and/or recirculated nitrated aromatic organic compounds (nitroaromatics) brings about a lowering of the interfacial tension between organic phase and acid phase and/or the amount of added and/or recirculated nitrated aromatic organic compounds (nitroaromatics) brings about improved dispersibility, in particular emulsifiability, of organic phase and acid phase.

Similarly, in a further particular embodiment of the present invention, the amount of nitrated aromatic organic compounds (nitroaromatics) added and/or recirculated for the conversion and/or nitration reaction can be selected in such a way that the proportion by weight of added and/or recirculated nitrated aromatic organic compounds (nitroaromatics), based on the nitratable aromatic organic compounds (aromatics) to be nitrated and/or reacted, is or varies in the range from 0.01 to 60% by weight, in particular in the range from 0.1 to 50% by weight, preferably in the range from 5 to 45% by weight, particularly preferably in the range from 10 to 40% by weight.

Likewise, in a further particular embodiment of the present invention, the amount of nitrated aromatic organic compounds (nitroaromatics) added and/or recirculated for the conversion and/or nitration reaction can be selected in such a way that the proportion by weight of added and/or recirculated nitrated aromatic organic compounds (nitroaromatics), based on the sulfuric acid of the nitric acid/sulfuric acid nitrating acid mixture, is in the range from 0.01 to 10% by weight, in particular in the range from 0.2 to 5% by weight, preferably in the range from 0.5 to 3% by weight, particularly preferably in the range from 1 to 2% by weight.

The process of the invention is also flexible in respect of the other process conditions and can be adapted or matched in virtually any way to the respective conditions (e.g. circumstances in respect of apparatus).

Thus, the introduction of nitrated aromatic organic compounds (nitroaromatics) can also be carried out in a variety of process stages and positions of the process of the invention. In particular, the nitrated aromatic organic compounds (nitroaromatics) added and/or recirculated for the conversion and/or nitration reaction can be added and/or introduced at least one of the following positions (i) to (iv): (i) the starting reaction mixture of all other reactants; and/or (ii) the sulfuric acid of the nitric acid/sulfuric acid nitrating acid mixture, in particular before production of the nitric acid/sulfuric acid nitrating acid mixture; and/or (iii) the nitric acid/sulfuric acid nitrating acid mixture; and/or (iv) the nitratable aromatic organic compounds (aromatics) to be nitrated. Combinations of two or more of these variants are in principle also possible.

Furthermore, the taking-off of nitrated aromatic organic compounds (nitroaromatics) to be recirculated can also be carried out in a variety of process stages and positions of the process of the invention. In particular, the nitrated aromatic organic compounds (nitroaromatics) added and/or recirculated for the conversion and/or nitration reaction can originate from at least one of the following positions (i) to (iv): (i) the crude nitrated aromatic organic compounds (crude nitroaromatics), preferably after removal of the acidic aqueous phase (acid phase) and/or after phase separation of the nitration mixture obtained into spent nitrating acid and crude nitrated aromatic organic compounds (crude nitroaromatics); and/or (ii) the scrubbed nitrated aromatic organic compounds (nitroaromatics), in particular after the acid or neutral scrub; and/or (iii) the nitrated aromatic organic compounds (nitroaromatics) which have been scrubbed, in particular obtained after the acid or neutral scrub, and stripped or distilled or dried; and/or (iv) the nitrated aromatic organic compounds (nitroaromatics) obtained in the vapor condensate after concentration of the spent nitrating acid. Here too, combinations of two or more of these variants are in principle possible.

In a particular embodiment of the present invention, the nitrated aromatic organic compounds (nitroaromatics) added and/or recirculated for the conversion and/or nitration reaction can advantageously be introduced into and/or added to both the organic phase and the acid phase of the starting reaction mixture. In this way, a particularly rapid and efficient partition equilibrium of the added and/or recirculated nitrated aromatic organic compounds (nitroaromatics) in the two abovementioned phases (organic phase and acid phase) is brought about. In this embodiment, it is also possible for, in particular, from 0.1 to 35% by weight, in particular from 10 to 25% by weight, based on the organic phase, of nitrated aromatic organic compounds (nitroaromatics) to be added to the organic phase and/or for from 0.01 to 3% by weight, in particular from 0.1 to 2% by weight, preferably from 0.5 to 1.5% by weight, particularly preferably from 1.1 to 1.5% by weight, based on the acid phase, of nitrated aromatic organic compounds (nitroaromatics) to be added to the acid phase.

In a particular embodiment of the process of the invention, it is possible, in particular, for the spent nitrating acid obtained after the conversion and/or nitration reaction to be, after removal of the crude nitrated aromatic organic compounds (crude nitroaromatics) and after the subsequent concentration and optionally addition of fresh nitric acid and/or sulfuric acid, recycled and/or circulated and/or recirculated to the nitration reaction, with the nitrated aromatic organic compounds (nitroaromatics) added and/or recirculated for the conversion and/or nitration reaction being added to and/or introduced into the concentrated spent nitrating acid which has optionally been admixed with fresh nitric acid and/or sulfuric acid and/or the nitratable aromatic organic compounds (aromatics) to be nitrated. In particular, the nitratable aromatic aromatic organic compounds (aromatics) can, in this particular embodiment, preferably be added and/or introduced immediately before commencement of the reaction and/or as last, on a time basis, reaction component (reactant), preferably immediately before the initial dispersing operation which triggers the conversion and/or nitration reaction.

In another further particular embodiment of the process of the invention, it is possible, in particular, for the spent nitrating acid obtained after the conversion and/or nitration reaction to be, after removal of the crude nitrated aromatic organic compounds (crude nitroaromatics) and after subsequent concentration, recycled as recycle acid and/or circulated and/or recirculated to the nitration reaction, giving firstly a dispersion of concentrated recycle acid and nitratable aromatic organic compounds (aromatics) to be nitrated and also nitrated aromatic organic compounds (nitroaromatics), with nitric acid subsequently being added to the dispersion, in particular dispersed therein, and the nitration reaction being initiated in this way. In particular, the nitric acid can, in this particular embodiment, preferably be added and/or introduced immediately before commencement of the reaction and/or as last, on a time basis, reaction component (reactant), preferably immediately before the first dispersing operation which triggers the conversion and/or nitration reaction.

As indicated above, the process of the invention is flexible in respect of the process conditions and can be adapted or matched in virtually any way to the respective conditions (e.g. circumstances in terms of apparatus). In this context, the (reaction) start temperature can also vary within a wide range.

The initial temperature for the conversion and/or nitration reaction can usually be selected in a temperature range from 70° C. to 120° C., in particular from 80° C. to 120° C., preferably from 80° C. to 110° C., particularly preferably from 85° C. to 105° C.

As indicated above in connection with the advantages and special aspects of the process of the invention, it is possible, in an advantageous embodiment of the process of the invention, for the initial temperature for the conversion and/or nitration reaction to be not more than 120° C., in particular not more than 100° C., preferably not more than 95° C., particularly preferably not more than 90° C.

In particular, the process of the invention leads to the nitration reaction also being able to be started at lower initial temperatures compared to the prior art (and without longer reaction or residence times than in processes according to the prior art with higher initial temperatures but otherwise the same conditions being required). In particular, the process of the invention enables the nitration to be initiated or started even at (reaction) start temperatures below 100° C., preferably below 95° C., particularly preferably below 90° C., without longer reaction or residence times than in processes according to the prior art having higher initial temperatures but otherwise the same conditions being required.

As regards the nitric acid/sulfuric acid nitrating acid mixture used according to the invention as nitrating agent, this can be, in particular, an aqueous nitric acid/sulfuric acid nitrating acid mixture.

The nitric acid/sulfuric acid nitrating acid mixture used usually contains, based on the nitric acid/sulfuric acid nitrating acid mixture, sulfuric acid in amounts of from 60 to 79% by weight, in particular from 62 to 75% by weight, preferably from 65 to 72% by weight, and nitric acid in amounts of from 1 to 8% by weight, in particular from 2 to 6% by weight, preferably from 3 to 5% by weight. The remainder to make up 100% by weight is water.

In a particular embodiment of the process of the invention, the nitric acid/sulfuric acid nitrating acid mixture can, in particular, be used in such amounts that the stoichiometric ratio of nitratable aromatic organic compounds (aromatics) to be nitrated to nitric acid present in the nitric acid/sulfuric acid nitrating acid mixture used is in the range from 1.0 to 1.5, in particular in the range from 1.05 to 1.15.

According to an advantageous embodiment of the process of the invention, the nitric acid/sulfuric acid nitrating acid mixture can, in particular, be used in such amounts that the volume-based phase ratio of spent nitrating acid to nitrated organic compounds (nitroaromatics) is in the range from 3:1 to 25:1, in particular in the range from 4:1 to 15:1, preferably in the range from 5:1 to 8:1.

According to a usual procedure, the process of the invention or the conversion and/or nitration reaction can be carried out in a reactor, in particular tube reactor.

In an embodiment of the process of the invention, the process or the conversion and/or nitration reaction can, in particular, be carried out in a reactor, in particular tube reactor, with the reaction time and/or the residence time of the reaction mixture in the reactor, in particular tube reactor, being selected in such a way that the nitric acid of the nitric acid/sulfuric acid nitrating acid mixture is reacted to an extent of at least 98%, in particular at least 99%, preferably at least 99.5%.

In a further embodiment of the process of the invention, the process or the conversion and/or nitration reaction can, in particular, be carried out in a tube reactor. Here, the reaction time and/or the residence time of the reaction mixture in the tube reactor can be from 10 to 180 seconds, in particular from 30 to 180 seconds, preferably from 40 to 120 seconds, particularly preferably from 60 to 90 seconds. Furthermore, this embodiment can be carried out in such a way that the reaction time and/or the residence time of the reaction mixture in the tube reactor does not exceed 180 seconds, in particular 120 seconds. Furthermore, the flow velocity of the reaction mixture in the tube reactor can, in this embodiment, be selected so that plug flow, in particular without backmixing, is present. In particular, the reaction mixture can, in this embodiment, flow through the tube reactor with plug flow, in particular without backmixing. In particular, the flow velocity of the reaction mixture in the tube reactor can be from 0.01 to 10 m/s, in particular from 0.1 to 5 m/s, preferably from 0.2 to 3 m/s, particularly preferably from 0.5 to 2 m/s, even more preferably from 0.8 to 1.5 m/s.

In a particular embodiment of the process of the invention, the process or the conversion and/or nitration reaction can, in particular, be carried out in a tube reactor, with the tube reactor being equipped with one or more, preferably more than one, mixing element(s) (dispersing elements), in particular for introducing additional mixing energy. In this embodiment, the mixing elements can, in particular, be configured as metal plates, in particular impingement or deflection plates, as orifice plates, as static mixers or as flow dividers. In particular, it can be provided for a mixing energy of from 10 to 1000 joule/liter, preferably from 10 to 500 joule/liter, particularly preferably from 20 to 200 joule/liter, to be introduced by the mixing elements. Furthermore, the pressure drop per mixing element can, in particular, be from 0.1 bar to 3.0 bar, preferably from 0.3 to 1.5 bar, particularly preferably from 0.3 to 0.8 bar. In this embodiment, preference can be given to the mixing elements being arranged in the tube reactor in such a way that the conversion of the nitric acid of the nitric acid/sulfuric acid nitrating acid mixture is at least 40%, in particular at least 50%, preferably at least 60%, in the first 10 to 30% by volume of the reactor. In this embodiment, preference can likewise be given to the mixing elements being arranged in the tube reactor in such a way that the conversion of introduced nitric acid at the end of the tube reactor is at least 98%, preferably at least 99%, particularly preferably at least 99.5%. Finally, according to a further particular embodiment of the process of the invention, the process or the conversion and/or nitration reaction can be carried out in a reactor, in particular tube reactor, wherein a dispersing device, preferably a mixing device, in particular for producing a dispersion or emulsion, in particular the starting reaction mixture or the nitration mixture, is located upstream of the reactor, in particular tube reactor. In this embodiment, the dispersing device, in particular the mixing device, can be configured as a stirred vessel, a jet mixer or a pump, in particular a centrifugal pump. In a particular variant of this embodiment, the dispersing device, in particular the mixing device, can be configured as a pump, in particular a centrifugal pump. In another particular variant of this embodiment, the dispersing device, in particular the mixing device, can be configured as a jet mixer; in particular, the jet mixer can produce a preferably central driving jet and a medium surrounding the driving jet, in particular in the form of an annular jet. In particular, the dispersing device, in particular the mixing device, can, in this embodiment, be located upstream, preferably directly upstream, of the reactor, in particular tube reactor, in particular with the dispersing device going over into the reactor or else, in particular, the dispersing device being integrated into the reactor and/or being a constituent of the reactor.

The process of the invention is particularly preferably carried out as follows, with the process being described by way of example for the nitration of benzene to give nitrobenzene. However, the process of the invention can, in particular, also be employed for all other aromatics which are difficult to disperse in sulfuric acid or nitrating acid (e.g. toluene, xylenes, chlorobenzenes, etc.).

The process underlying an adiabatic nitration of benzene to give nitrobenzene and the reactor used for this purpose are described by way of example in EP 1 272 268 A2, in EP 1 291 078 A2 and in EP 2 168 942 A1.

In an adiabatic nitration, as is also preferably employed in the process of the invention, it is quite generally possible to mix a mixed acid (nitrating acid mixture or nitrating acid), typically having, for example, a proportion by weight of sulfuric acid of from 60 to 79% by weight, in particular from 62 to 75% by weight, preferably from 65 to 72% by weight, and having a proportion by weight of nitric acid of from 1 to 8% by weight, preferably from 2 to 6% by weight, particularly preferably from 3 to 5% by weight, with the benzene to be nitrated, preferably in a stoichiometric ratio of benzene to nitric acid of from 1.0 to 1.5, preferably from 1.05 to 1.15, in a dispersing apparatus. The phase ratio between organic phase and acid phase in the nitration mixture is determined by the concentration of nitric acid in the mixed acid used: in the case of a mixed acid containing 4.5% by weight of nitric acid, there is, at an excess of benzene of 10% on a weight basis, a ratio of mixed acid/benzene of 16.3. At the end of the reaction, a nitration mixture, in which the total heat of reaction is stored, having a ratio of spent acid/product of about 10.3 is then obtained. The temperature rise in the nitration mixture, i.e. the difference ($\Delta T$) between final temperature and initial temperature, is determined unambiguously by the phase ratio in a conversion of nitric acid into product of more than 99%. If the phase ratio becomes smaller, e.g. due to a higher content of nitric acid in the mixed acid, the difference ($\Delta T$) between final temperature and initial temperature becomes greater, and vice versa.

After mixing of the reaction participants the two-phase mixture of organic phase and acid phase is dispersed in such a way that the nitration starts, e.g. in a tube reactor, which can be recognized from a steep temperature increase in the nitration mixture. The initial temperature is given by the mixing temperature of the individual feedstreams and in the case of an adiabatic nitration, in particular of benzene to give nitrobenzene, is typically in the range from 70 to 120° C., in particular in the range from 80 to 120° C., preferably in the range from 80 to 110° C., particularly preferably in the range from 85 to 105° C. In particular, the initial temperature for the conversion and/or nitration reaction is not more than 120° C., in particular not more than 100° C., preferably not more than 95° C., particularly preferably not more than 90° C.

The residence time of the nitration mixture in the tube reactor, in which at least 98%, preferably more than 99%, of the nitric acid introduced has been reacted at the end, can usually be from 30 to 180 seconds, preferably not more than 120 seconds, particularly preferably from 60 to 90 seconds. The flow velocity of the nitration mixture in the tube can be from 0.1 to 5.0 m/s, preferably from 0.2 to 3.0 m/s, particularly preferably from 0.5 to 2.0 m/s, very particularly preferably from 0.8 to 1.5 m/s, so that plug flow without backmixing prevails in the tube reactor. The dimensioning of the tube reactor is definitely fixed by setting of an hourly output of product, a content of nitric acid in the mixed acid, residence time and flow velocity in the tube reactor.

In a particular embodiment, the mixed acid can preferably be produced at the beginning by combining sulfuric acid and nitric acid. In a second step, the aromatic to be nitrated can then be dispersed in this mixed acid. The initial temperature then results as the mixing temperature of the individual feedstreams. The temperatures of the feedstreams are preferably set in such a way that the desired initial temperature prevails after mixing.

Apart from selection of a suitable initial temperature, setting of the temperature difference ($\Delta T$) between final temperature and initial temperature and also the final temperature of the nitration mixture itself, a further prerequisite for largely complete conversion of the nitric acid with adherence to the prescribed residence times is dispersion of the aromatic to be nitrated in the mixed acid so that the nitration commences in such a way that the desired temperature rise occurs in the nitration mixture (which will be known and familiar to a person skilled in the art from the prior art) immediately after the first dispersing operation carried out in a targeted way. For this purpose, the aromatic to be nitrated can be dispersed in the mixed acid, e.g. by means of appropriately shaped nozzles (cf., for example, EP 0 373 966 A2, EP 0 436 443 A2 or EP 0 708 076 A2), or the nitration mixture can be dispersed for the first time by means of static mixers (cf., for example, EP 0 489 211 A1 or EP 0 779 270 A1) or by means of jet mixers (cf., for example, EP 0 771 783 A1) or by use of specifically shaped orifice plates (cf., for example, EP 1 272 268 A2 or EP 1 291 078 A2), which are preferably also used in the redispersing operation.

Regardless of the dispersing technique used, in the first dispersing of the phases in one another, e.g. of benzene in the mixed acid which is present in a large excess, the most unfavorable interfacial tensions prevail between the phases, as a result of which optimal dispersing is hindered. In addition, the dispersions of the pure aromatic to be nitrated in mixed acid produced by energy input tend to coalesce rapidly.

The interfacial tensions between nitroaromatic and aqueous phase (e.g. nitrobenzene and water) are significantly lower than the interfacial tensions between the aromatic to be nitrated (e.g. benzene) and water. The addition according to the invention of the nitrated product before the first initial dispersing operation which triggers the reaction efficiently and significantly reduces the interfacial tensions at the phase interfaces, as a result of which improved dispersing is achieved at the beginning and the tendency for the dispersion initially produced to coalesce is reduced.

In the additional addition provided for according to the invention of the nitrated product as further component in addition to sulfuric acid, nitric acid and aromatic to be nitrated (e.g. benzene) to the nitration mixture before commencement of the nitration, preferably for adiabatic nitration in a tube reactor, in particular shortly before commencement of the reaction, i.e. before the first initial dispersing operation which triggers the nitration, various variants in the order of the addition are possible. The product to be recirculated can, in particular, be introduced a) into the concentrated and recycled sulfuric acid (recycle acid) before addition of the aromatic to be nitrated (e.g. benzene) and before mixing-in of the nitric acid and/or b) into the mixed acid before addition of the aromatic to be nitrated (e.g. benzene) shortly after mixing-in of the nitric acid and/or c) together with the aromatic to be nitrated and/or d) as substream of the nitration emulsion before phase separation into the recycle acid or mixed acid and/or e) as a combination of a) to c), in particular in such a way that part of the added nitrated product (e.g. nitrobenzene) is introduced into the aqueous phase as per a) and/or b) and another part is introduced together with the aromatic to be nitrated as per c).

The addition of the aromatic to be nitrated as second reactive component in the nitration mixture apart from the nitric acid is advantageously carried out in cases a) to e) always, in particular, at the end, preferably shortly before the first dispersing operation which triggers the reaction.

Apart from these variants, in particular also addition of the aromatic to be nitrated to the nitration mixture as last component before the first dispersing operation, it is particularly advantageous to add the nitric acid as second partner participating in the nitration as last component before the first dispersing operation to the nitration mixture.

It has been found to be advantageous for homogeneous mixing with the recycle acid (in the case of nitric acid) or predispersion in the recycle sulfuric acid (in the case of recirculated nitrated product or aromatic to be nitrated) to be effected by means of suitable mixing devices (e.g. static mixers, orifice plates, jet mixers, etc.) in such a way that only a small pressure drop occurs at these mixing devices after each introduction of a starting material into the concentrated recycle sulfuric acid, the main component of the nitration mixture.

The product (e.g. nitrobenzene) added to the concentrated recycle acid, mixed acid or the aromatic to be nitrated (e.g. benzene) can equally well be taken from various stages of the process, i.e.

A) as crude nitrobenzene, in particular after phase separation of the nitration mixture composed of spent nitrating acid and nitrobenzene, before or after cooling and preferably before treatment with a scrubbing medium (this crude nitrobenzene contains, in addition to the product, from 2 to 10% of benzene, nitrophenols and traces of sulfuric acid in dissolved form, from about 0.2 to 0.25%, and spent acid as microemulsion, but no water); and/or B) as partially purified nitrobenzene, free of acids, after the acid scrub (this nitrobenzene from the acid scrub contains, in addition to the total nitrophenols, all the excess benzene and is saturated with water); and/or C) as purified nitrobenzene after the neutral scrub (this nitrobenzene from the neutral scrub contains only traces of nitrophenols, from about 2 to 60 ppm, and all the excess benzene and is likewise saturated with water); and/or D) as the nitrobenzene obtained in the vapor condensate in the concentration of the spent acid to recycle acid (this nitrobenzene, about 10-15% of the product, from the condensate of the concentration of the spent acid is substantially free of nitrophenols but likewise still contains small residues of benzene and is likewise saturated with water) and/or E) as final product, after removal of the excess of benzene, water-free or saturated with water; and/or F) also as a partial offtake of nitration emulsion before the phase separation with subsequent recirculation to the nitration process; and/or G) combinations of A) to F).

The recirculation of a nitrobenzene still containing benzene after the abovementioned positions A) to C) is advantageous and that of a nitrobenzene still containing benzene after the abovementioned positions B) and C) is particularly advantageous in order to minimize the formation of by-products, especially dinitrobenzene from nitrobenzene, with traces of nitric acid in the recycle acid.

In the case of addition of the product to a recycle acid which has been concentrated before addition of the nitric acid or to mixed acid, from, in particular, 0.1 to 5.0% by weight, preferably from 0.5 to 3.0% by weight, particularly preferably from 1.1 to 2.0% by weight, is added to the recycle acid.

An efficient lowering of the interfacial tension between the organic phase and the acid phase is likewise achieved by admixing the benzene to be nitrated with nitrobenzene in such a way that a mixture of benzene/nitrobenzene comprising from 0.1 to 50%, preferably from 5.0 to 45%, particularly preferably from 11 to 40%, of nitrobenzene is introduced.

Both in the case of addition of the nitrated product (e.g. nitrobenzene) directly to the recycle acid and also in the case of addition of the product (e.g. nitrobenzene) to the aromatic to be nitrated, it is advantageous to provide predispersion of the nitrated product or of the mixture of nitrated product/aromatic to be nitrated and a certain residence time, whose duration depends on the quality of the predispersing of the added organic phases in the recycle acid, so that a partition equilibrium of nitrated product between acid and organic phase can be established before the optimally altered interfacial tension between the two phases containing nitrated product becomes effective.

To shorten this residence time before the first dispersing operation, it is particularly advantageous to add nitrated product (e.g. nitrobenzene) to the recycle acid or mixed acid in such an amount that the solubility limit for the added product in the respective acid is exceeded. A mixture of nitrated product/acid consisting of two phases is then formed.

In the addition of the aromatic to be nitrated to this mixture, the part of the added nitrated product which is not dissolved in the acid is immediately mixed with the aromatic to be nitrated, so that a mixture of benzene/nitrobenzene results as organic phase even before the first dispersing operation. Both phases, which each contain nitrobenzene, in this way contribute to the reduced interfacial tension desired for the first dispersing operation.

A further possible way of shortening the residence time in the tube reactor before the first dispersing operation and thus for attaining an approximate partition equilibrium for the added product between the two phases more quickly is to introduce the product (e.g. nitrobenzene) into the nitration circuit both via the acid phase and also via the organic phase, especially in such a way that, for example, from 0.1 to 2.0% by weight, preferably from 0.5 to 1.5% by weight, particularly preferably from 1.1 to 1.5% by weight, based on the amount of recycle acid, can be added to the acid phase and/or that, for example, from 0.1 to 32% by weight, preferably from 11.0 to 25% by weight, of nitrobenzene can be added to the organic phase composed of benzene to be nitrated and nitrobenzene.

Apart from the variant of addition of the aromatic to be nitrated as last component before the first dispersing operation of the complete nitration mixture, as described above, it can equally well be advantageous firstly to predisperse the mixture of recycle acid, nitrated product and aromatic to be nitrated and subsequently add the nitric acid as last component to the nitration mixture, especially in such a way that not only is the nitric acid uniformly dispersed homogeneously in the aqueous phase in fractions of seconds by means of suitable mixing devices and the predispersed nitration mixture is not only retained but additional further dispersing and, associated therewith, an even greater exchange area between disperse organic phase and homogeneous acid phase is produced.

The above invention or the process of the invention can in principle be used for any adiabatic nitration processes known from the prior art, preferably for adiabatic nitration processes in conjunction with a tube reactor in which the nitration using pure starting materials, in particular the difficult-to-disperse aromatic (preferably benzene) and a pure mixed acid (aqueous nitric acid/sulfuric acid nitrating acid mixture), is started by introduction of mechanical mixing energy, as described, for example, in EP 0 373 966 A2, in EP 0 436 443 A2, in EP 0 489 211 A1, in EP 0 708 076 A2, in EP 0 771 783 A1, in EP 0 779 270 A1, in EP 1 272 268 A2, in EP 1 291 078 A2, in EP 2 168 942 A1, in EP 2 354 117 A1 and in EP 2 473 477 A1.

The present invention further provides, according to a second aspect of the present invention, a production plant (i.e. nitration plant or plant) for the nitration, in particular adiabatic nitration, of nitratable aromatic organic compounds (aromatics) to give nitrated products in the form of the corresponding nitrated aromatic organic compounds (nitroaromatics), in particular a production plant for carrying out a process according to the present invention as described above, wherein the production plant comprises the following units and apparatuses:
(a) a nitration unit for the nitration, in particular adiabatic nitration, of nitratable aromatic organic compounds (aromatics) to give nitrated products in the form of the corresponding nitrated aromatic organic compounds (nitroaromatics), in particular having one or more reactors for carrying out the nitration reaction, preferably a tube reactor;
(b) optionally, arranged downstream of the nitration unit in the production line, at least one separation apparatus, in particular a separating apparatus (separator), in particular for separating the spent nitrating acid from the nitrated crude products;
(c) arranged downstream of the nitration unit and of any separation apparatus present in the production line, at least one scrubbing unit for carrying out a scrub of the nitrated crude products with a scrubbing medium, in particular in one or more scrubbing steps;
(d) arranged downstream of the scrubbing unit in the production line, a separation apparatus, in particular a separating apparatus (separator), for separating the scrubbed nitrated products from the scrubbing medium;
where the production plant additionally comprises at least one recirculation device for partial recirculation of the nitrated products to the nitration unit, in particular into the starting reaction mixture of the nitration unit.

In a preferred embodiment of the present invention, the nitration unit comprises at least one tube reactor as reactor.

In particular, the nitration unit can, in a preferred embodiment of the production plant of the invention, comprise at least one tube reactor as reactor, where the tube reactor is equipped with one or more, preferably a plurality of, mixing elements (dispersing elements), in particular for the introduction of additional mixing energy. In this embodiment, the mixing elements can, in particular, be configured as metal plates, in particular impingement or deflection plates, as orifice plates, as static mixers or as flow dividers. Furthermore, it is possible in this embodiment for the mixing elements to be, in particular, configured in such a way that in the operating state a mixing energy of from 10 to 1000 joule/liter, preferably from 10 to 500 joule/liter, particularly preferably from 20 to 200 joule/liter, is introduced by the mixing elements. Furthermore, the pressure drop per mixing element in the operating state can be from 0.1 bar to 3.0 bar, preferably from 0.3 to 1.5 bar, particularly preferably from 0.3 to 0.8 bar, in this embodiment. Furthermore, in a particular variant of this embodiment, the mixing elements can be arranged in the tube reactor in such a way that in the operating state the conversion of the nitric acid of the nitric acid/sulfuric acid nitrating acid mixture is at least 40%, in particular at least 50%, preferably at least 60%, in the first 10 to 30% by volume of the reactor. Finally, in a particular variant of this embodiment, the mixing elements can be arranged in the tube reactor in such a way that the conversion of nitric acid introduced is at least 98%, preferably at least 99%, particularly preferably at least 99.5%, at the end of the tube reactor.

Furthermore, according to a particular embodiment of the production plant of the invention, a dispersing device, preferably a mixing device, in particular for producing a dispersion or emulsion, in particular the starting reaction mixture or the nitration mixture, can be located upstream of the reactor or reactors, in particular tube reactor, of the nitration unit.

In this embodiment, the dispersing device, in particular the mixing device, can be configured as a stirred vessel, a jet mixer or a pump, in particular a centrifugal pump. In a particular variant of this embodiment, the dispersing device, in particular the mixing device, can be configured as a pump, in particular a centrifugal pump. In another particular variant of this embodiment, the dispersing device, in particular the mixing device, can be configured as a jet mixer, in particular with the jet mixer producing a preferably central driving jet and a medium surrounding the driving jet, in particular in the form of an annular jet. In this embodiment, the dispersing device, in particular the mixing device, can, in particular, be located upstream, preferably directly upstream, of the reactor, in particular tube reactor, especially with the dispersing device going over into the reactor or else, in particular, with the dispersing device being integrated into the reactor and/or being a constituent of the reactor.

As regards the scrubbing unit arranged downstream of the nitration unit in the production line and any separation apparatus present, this scrubbing unit can typically comprise
    at least one dispersing device, in particular at least one mixing device, for contacting and emulsifying the nitrated crude products and a scrubbing medium and,
    arranged downstream of the dispersing device, a tube reactor for feeding in the emulsion of nitrated crude products and scrubbing medium produced in the dispersing device; in particular with the tube reactor being configured in such a way that removal of the impurities initially present in the nitrated crude products during passage of the emulsion through the tube reactor is made possible and/or that the impurities initially present in the nitrated crude products are transferred into the scrubbing medium during passage of the emulsion through the tube reactor and/or neutralized thereby.

It goes without saying that conventional scrubbing devices (e.g. mixer/settler apparatus, extraction columns, etc.) can additionally be present.

The scrubbing unit can usually be configured for carrying out the scrub in at least two scrubbing steps, in particular at least one acid scrub and at least one neutral scrub.

In a preferred embodiment, the scrubbing unit (W) can, in particular, be configured for carrying out a scrub having at least three scrubbing steps. In particular, the scrub comprising at least three scrubbing steps can comprise: (i) at least one first scrubbing step carried out in an acid medium ("acid scrub"), preferably using water or a mineral acid as scrubbing medium, (ii) at least one second scrubbing step carried out in an alkali (basic) medium ("basic scrub"), preferably using a base as scrubbing medium, and (iii) at least one third scrubbing step carried out in a neutral medium ("neutral scrub"), preferably using water as scrubbing medium.

As explained above in connection with the process of the invention, the process of the invention is flexible in respect of the process conditions and can be adapted in virtually any way to the respective conditions (e.g. conditions in terms of apparatus). Thus, as indicated above, the introduction and offtake of nitrated aromatic organic compounds (nitroaromatics) can, in particular, be effected in a variety of process stages and positions of the process of the invention. This also applies to the production plant of the invention.

Thus, the recirculation device provided in the production plant of the invention for partial recirculation of the nitrated products to the nitration unit can, in a particular embodiment of the present invention, be configured and/or arranged in such a way that, in particular, the nitrated products to be partially recirculated are taken from at least one of the following positions (i) to (iv) of the production stream: (i) the crude nitrated aromatic organic compounds (crude nitroaromatics), preferably after removal of the acidic aqueous phase (acid phase) and/or after phase separation of the nitration mixture obtained into spent nitrating acid and crude nitrated aromatic organic compounds (crude nitroaromatics); and/or (ii) the scrubbed nitrated aromatic organic compounds (nitroaromatics), in particular after the acid or neutral scrub; and/or (iii) the nitrated aromatic organic compounds (nitroaromatics) which have been scrubbed, in particular obtained after the acid or neutral scrub, and been stripped or distilled or dried; and/or (iv) the nitrated aromatic organic compounds (nitroaromatics) obtained in the vapor condensate after concentration of the spent nitrating acid. In principle, combinations of two or more of these variants are also possible.

Furthermore, the recirculation device provided in the production plant of the invention for the partial recirculation of the nitrated products to the nitration unit can, in a further particular embodiment of the present invention, be configured and/or arranged in such a way that, in particular, the nitrated products to be partially recirculated are added and/or introduced at least one of the following positions (i) to (iv) of the production stream: (i) the starting reaction mixture of all other reactants; and/or (ii) the sulfuric acid of the nitric acid/sulfuric acid nitrating acid mixture, in particular before producing the nitric acid/sulfuric acid nitrating acid mixture; and/or (iii) the nitric acid/sulfuric acid nitrating acid mixture; and/or (iv) the nitratable aromatic organic compounds (aromatics) to be nitrated. In principle, combinations of two or more of these variants are also possible here.

Finally, the production plant can, in a further particular embodiment of the production plant of the invention, additionally comprise at least one recycling device for recycling the spent nitrating acid. In this way, the process economics and process efficiency can be improved further. In particular, the recycling device can, in this particular embodiment, comprise a device for concentrating the spent nitrating acid and optionally a device for adding fresh nitric acid and/or sulfuric acid.

As regards further details of the production plant of the invention, reference may be made to what has been said above in respect of the process of the invention, which applies analogously to the production plant of the invention, in order to avoid unnecessary repetition.

The present invention further provides, according to a third aspect of the present invention, for the use of nitrated aromatic organic compounds (nitroaromatics) as dispersant (dispersing agent), in particular emulsifier, for nitrations, in particular for nitration reactions of the corresponding unnitrated aromatic organic compounds.

Furthermore, the present invention further provides, according to this aspect of the invention, for the use of nitrated aromatic organic compounds (nitroaromatics) for lowering the interfacial tension of organic phase and acid phase and/or for improving the dispersibility of organic phase and acid phase in nitrations, in particular in nitration reactions of the corresponding unnitrated aromatic organic compounds.

Finally, the present invention further provides, according to this aspect of the invention, for the use of nitrated aromatic organic compounds (nitroaromatics) for increasing the yields and/or for reducing by-product formation and/or for shortening the total reaction times and/or for lowering the reaction start temperatures in nitrations, in particular in nitration reactions of the corresponding unnitrated aromatic organic compounds.

In the context of the uses according to the invention, the following procedure can generally be employed: nitratable aromatic organic compounds (aromatics) are converted in a preferably adiabatic nitration reaction with a nitric acid/sulfuric acid nitrating acid mixture into the corresponding nitrated aromatic organic compounds (nitroaromatics); wherein corresponding nitrated aromatic organic compounds (nitroaromatics) are added to the starting reaction mixture which comprises the nitratable aromatic organic compounds (aromatics) and the nitric acid/sulfuric acid nitrating acid mixture and the conversion and/or nitration reaction is started and/or carried out in the presence of the nitrated aromatic organic compounds (nitroaromatics); and/or wherein the nitrated aromatic organic compounds (nitroaromatics) obtained are partially recirculated to the nitration reaction and the subsequent conversion and/or nitration reaction is started and/or carried out in the presence of the nitrated aromatic organic compounds (nitroaromatics).

As regards further details of the uses according to the invention, reference may be made to what has been said above in respect of the process of the invention and in respect of the production plant of the invention, which applies analogously to the uses according to the invention, in order to avoid unnecessary repetition.

Further advantages, properties, aspects and features of the present invention may be derived from the following description of the pictorial presentations of embodiments preferred according to the invention as depicted in FIGS. 1, 2*a-d* and 3.

Figure 2A:
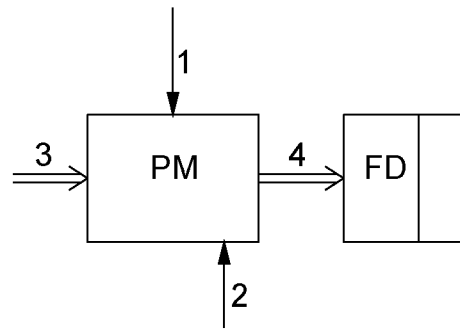
FIG. 2a-d further schematic depictions of various variants of the process of the invention or the production plant of the invention as per further preferred embodiments of the present invention (FIGS. 2b-c) compared to the prior art (FIG. 2a)
Figure 3:
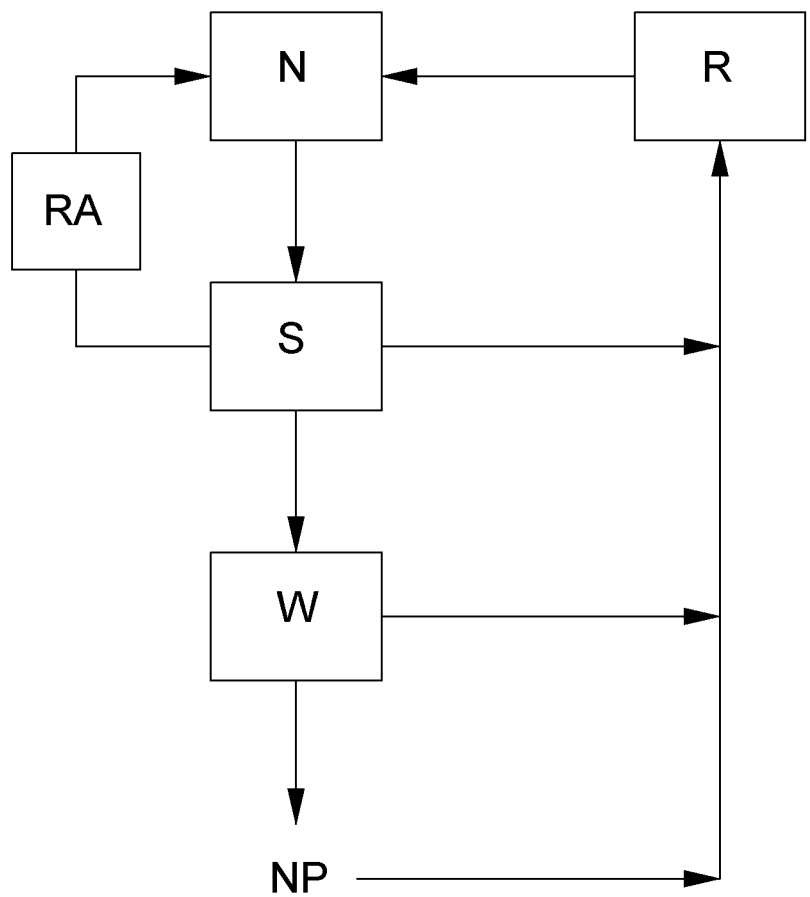
FIG. 3 another further schematic depiction of a process according to the invention or a production plant according to the invention as per a preferred embodiment of the present invention as per a further preferred embodiment of the present invention.

The figures show:

FIG. 1 a schematic depiction of a process according to the invention or a production plant according to the invention as per a preferred embodiment of the present invention;

FIG. 2*a-d* further schematic depictions of various variants of the process of the invention or the production plant of the invention as per further preferred embodiments of the present invention (FIGS. 2*b-c*) compared to the prior art (FIG. 2*a*);

FIG. 3 another further schematic depiction of a process according to the invention or a production plant according to the invention as per a preferred embodiment of the present invention as per a further preferred embodiment of the present invention.

Figure 2B:
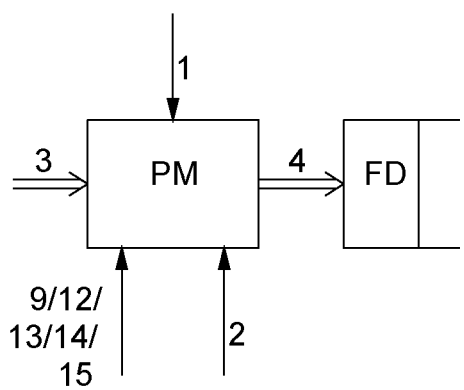
Figure 2C:
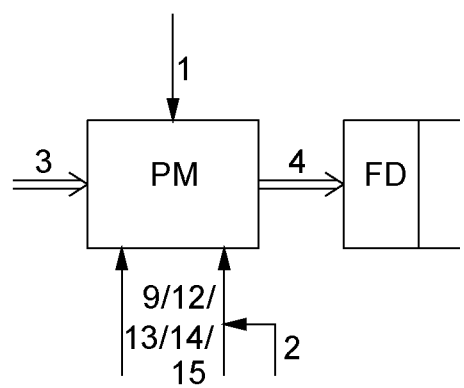
Figure 2D:
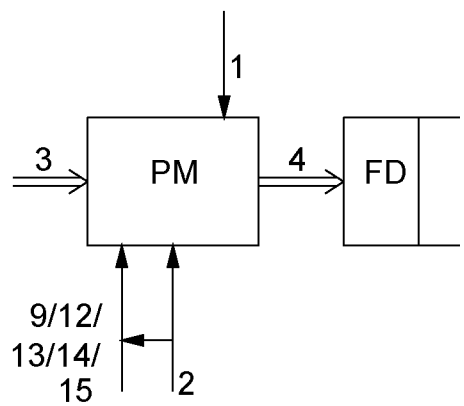

FIG. 1 schematically shows an embodiment of a process according to the invention for the various variants for recirculating product to the nitration mixture for the example of the nitration of benzene to give nitrobenzene, while FIGS. 2*b-d* schematically show the most important of the various possible variants and sequences for the addition of the various starting materials for the example of the nitration of benzene to give nitrobenzene.

As shown in FIG. 1, the starting materials nitric acid 1, benzene 2 and recirculated nitrobenzene 9, 12, 13, 14 and 15 are introduced in a prescribed or defined order (as shown in FIGS. 2*b-d*) in a metering/premixing unit PM of a tube reactor TR, which is directly connected to this tube reactor, into the concentrated recycle sulfuric acid 3 which is fed by means of a suitable pump P (e.g. centrifugal pump) at a defined admission pressure P1 (at least the sum of all pressure drops in the tube reactor plus final pressure P2) into the metering/premixing unit PM. The nitric acid dissolves completely and homogeneously in the recycle acid. The benzene 2 and the recirculated nitrobenzene 9, 12, 13, 14 or 15 together with the recycle acid (sulfuric acid)/nitric acid (=mixed acid) form an initial nitration mixture 4 consisting of two phases and are predispersed. The temperature in this nitration mixture 4 of mixed acid, benzene and nitrobenzene is determined as mixing temperature (i.e. the initial temperature) from the temperatures of the individual feedstreams (1, 2, 3 and/or 9, 12, 13, 14, 15) and is selected in a range from 80 to 120° C. in such a way that the nitration starts after the first dispersing operation in the dispersing device FD. These starting materials which have been premixed in the metering/premixing unit PM are subsequently dispersed in one another in the dispersing device FD in such a way that a sufficiently large exchange area (phase interface) between the organic phase and acid phase for the nitration to be initiated or to commence or start, which can be recognized from a very steep temperature rise in the nitration mixture 4 after the dispersing device FD, is formed. The decrease in the phase interface between organic phase and acid phase caused by coalescence during passage of the nitration mixture through the tube reactor TR is countered by further dispersing elements $RD_1$ to $RD_n$ distributed in the tube reactor TR. At the outlet of the tube reactor, the nitration mixture 5 (now a mixture of spent acid and product) goes at a final temperature usually in the range from 120 to 145° C. and a pressure P2 into the phase separation apparatus S. The pressure P2 is selected so that flash evaporation of the volatile components in the nitration mixture 5, especially in the crude nitrobenzene (a mixture of aliphatics/benzene/nitrobenzene in the case of the nitration of benzene to give nitrobenzene), in the phase separation apparatus is reliably avoided.

As also shown in FIG. 1, a substream 13 of the crude nitrobenzene 6, which contains sulfuric acid, as microemulsion and dissolved, also all impurities (e.g. unreacted benzene, nitrophenols, etc.), can, after phase separation in the phase separation apparatus S, be recirculated before or after cooling via the metering/premixing unit PM to the nitration. The main amount of the crude nitrobenzene 6 is freed of all acidic compounds (e.g. mineral acids, nitrophenols, etc.) in the scrub W by means of water (with and without addition of bases) in from one to three scrubbing steps. A substream 14 of this nitrobenzene/benzene mixture 7, branched off from one or more of the scrubbing steps of the scrub consisting of a plurality of scrubbing steps, is preferably recirculated to the nitration. The main amount of the nitrobenzene/benzene mixture 7, which is, except for traces, free of all mineral acids and nitrophenols, can subsequently be freed of the unreacted benzene 10 and of volatile aliphatic impurities, e.g. by distillation or stream stripping in the purification unit DS. The recovered benzene 10 is, after removal of the excess aliphatics, recirculated to the nitration. A substream 9 of the completely purified nitrobenzene 8 can likewise be recirculated to the nitration.

As finally shown in FIG. 1, the water originating from the nitration and the nitric acid and the nitrobenzene dissolved in the spent acid up to the solubility limit and also traces of further volatile components (e.g. benzene, nitric acid, aliphatics, etc.) can be completely removed at a temperature of from 120 to 145° C. (e.g. by flash evaporation in the evaporator AR) from the spent acid 11 separated off in the phase separation unit S. The vapor condensate obtained in the flash evaporation of the spent acid, which is a mixture of water and pure nitrobenzene 12 (which makes up from about 10% to 15% of the total nitrobenzene produced) is usually purified and further treated in the scrub together with the crude nitrobenzene 6 from the phase separation apparatus S. According to the process of the invention, this pure nitrobenzene 12 from the vapor condensate can, likewise after phase separation, be recirculated in its entirety to the nitration.

In addition, nitrobenzene from the nitration can be recirculated to the nitration circuit by recirculating a substream 15 of the nitration mixture 5, before phase separation.

A further variant which is not depicted of the process of the invention comprises recirculating nitrobenzene from the wastewater treatment, e.g. from wastewater stripping.

In respect of the pictorial depictions in FIGS. 2a-d, the following may be said in particular:

FIG. 2a shows, for comparison with the prior art for the usual sequence of the addition of the starting materials nitric acid and benzene to the recycle sulfuric acid: the nitric acid 1 is firstly added to the recycle acid 3 and homogeneously mixed with the recycle acid 3. The benzene 2 to be nitrated is added to the resulting mixed acid (streams 3+1) and the resulting starting nitration mixture 4 or the starting reaction mixture (mixed acid/benzene) is dispersed in the dispersing unit FD in such a way that a sufficiently large exchange area (phase interface) for the nitration to start, which can be recognized by a very steep temperature rise in the starting nitration mixture 4 after the dispersing device FD is formed.

In FIG. 2b, the starting materials nitric acid 1, benzene 2 and nitrobenzene from the various sources 9, 12, 13, 14 or 15 are, according to the invention, added to the recycle sulfuric acid in the order: nitrobenzene from the source 9, 12, 13, 14 or 15, then nitric acid 1 and finally benzene 2. The nitrobenzene can be predispersed in the recycle sulfuric acid 3 before addition of the nitric acid. The nitric acid is mixed in homogenously as quickly as possible, and after addition of the benzene to the mixture of mixed acid/nitrobenzene the starting nitration mixture 4 is dispersed in the dispersing device FD in such a way that a sufficiently large exchange area (phase interface) for the nitration to start, which can be recognized by a very steep temperature rise in the starting nitration mixture 4 after the dispersing device FD, is formed.

In FIG. 2c, the starting materials, nitric acid 1, benzene 2 and nitrobenzene from the various sources 9, 12, 13, 14 or 15, are added to the recycle sulfuric acid 3 in the order: nitrobenzene from the source 9, 12, 13, 14 or 15, nitric acid 1 and finally benzene 2, which is present as a mixture of benzene with nitrobenzene from the source 9, 12, 13, 14 or 15. The nitrobenzene can be predispersed in the recycle acid 3 before addition of the nitric acid. The nitric acid is mixed in homogenously as quickly as possible, and after addition of the benzene/nitrobenzene mixture to the mixture of mixed acid (nitrating acid)/nitrobenzene, the starting nitration mixture 4 is dispersed in the dispersing device FD in such a way that a sufficiently large exchange area (phase interface) for the nitration to start, which can be recognized by a very steep temperature rise in the starting nitration mixture 4 after the dispersing device FD, is formed.

Finally, in FIG. 2d the starting materials, i.e. nitric acid 1, benzene 2 and nitrobenzene from the various sources 9, 12, 13, 14 or 15, are added to the recycle sulfuric acid in the following order: addition of nitrobenzene from the source 9, 12, 13, 14 or 15, then benzene 2 alone and/or as mixture with nitrobenzene from the source 9, 12, 13, 14 or 15 or in separate streams to the recycle acid. The nitrobenzene/benzene mixture is predispersed in the recycle acid before addition of the nitric acid. The nitric acid is finally added and mixed in homogeneously as quickly as possible. This starting nitration mixture is dispersed in the dispersing device FD in such a way that a sufficiently large exchange area (phase interface) for the nitration to start or commence, which can be recognized by a very steep temperature rise in the starting nitration mixture 4 after the dispersing device FD, is formed.

FIG. 3 shows a further schematic depiction of the process of the invention or the inventive production plant according to the present invention as per a particular embodiment of the present invention: according to FIG. 3, the nitration, in particular under adiabatic conditions, of the nitratable aromatic organic starting compounds (aromatics) to give the corresponding nitrated aromatic organic compounds (nitroaromatics) firstly occurs in a nitration unit N according to the above-described reaction approach (i.e. starting reaction mixture composed of aromatic to be nitrated and nitric acid/sulfuric acid nitrating acid mixture and addition of corresponding nitrated product). Downstream of the nitration unit N in the production line, there is a separation device S, in particular a separating device (separator), for separating the spent nitrating acid or the spent nitrating acid mixture from the nitrated crude products. Downstream of the nitration unit N and of the separation device S in the production line, there is a scrubbing device W for carrying out a scrub of the nitrated crude products, as described above, so that the scrubbed and purified nitrated products NP are subsequently formed (after removal of the scrubbing medium and optionally drying of the scrubbed nitrated products).

The plant of the invention and process procedure as per FIG. 3 is, as described above, characterized in that a recirculation device R for partial recirculation of nitrated product to the starting reaction mixture is additionally provided so as to make the above-described process procedure according to the invention possible. Here, the recirculation device according to the invention is configured so that the nitrated product can be taken off at a variety of positions in the production plant of the invention or in a variety of positions in the process of the invention and be recirculated, as described in detail above (e.g. as two-phase nitration mixture directly after the nitration and/or as nitrated crude product after removal of the spent nitrating acid and/or before, from or after the scrub, in particular after the acid scrub or after the neutral scrub, and/or as pure nitrobenzene from the concentration of the spent nitrating acid in the recycling unit RA or as purified and optionally dried final nitrated product, with combinations of these possibilities also being able to be provided).

The partial recirculation of the nitrated product to the starting reaction mixture is associated with the advantages described in detail above, in particular with improving the dispersibility of organic phase and acid phase and thus with an improved overall reaction (i.e. improved yields, reduction in by-product formation, lower initial temperatures, improved energy efficiency, improved handleability, etc.).

As shown in FIG. 3 and explained above, the production plant can, in a further particular embodiment of the production plant of the invention, additionally comprise at least one recycling device RA for recycling the spent nitrating acid. In particular, as explained above, the recycling device RA can, in this particular embodiment, comprise a device for concentrating the spent nitrating acid and optionally a device for adding fresh nitric acid and/or sulfuric acid.

Overall, an improved nitration process for nitratable aromatic organic compounds and a corresponding (production) plant for carrying out this process, which display an overall improved efficiency, in particular an improved technical efficiency and also an improved energy efficiency, and overall improved process economics and also improved handleability, are therefore provided by the present invention.

Further embodiments, adaptations, variations, modifications or the like of the present invention can readily be recognized and realized by a person skilled in the art on reading the description, without going outside the scope of the present invention.

The present invention will be illustrated with the aid of the following working examples, but without the present invention being restricted thereto.

WORKING EXAMPLES

Example 1 (Comparative Example)

762 g/h of benzene (10% excess) and 15.4 kg/h of mixed acid having a content of sulfuric acid of 65.73% and of nitric acid of 4.99% are metered for an initial temperature of 80° C. into a tube reactor which has an internal volume of 231 ml and is equipped with 17 mixing elements (combination of static mixing elements and orifice plates) at unequal spacings. The benzene is introduced into the reactor at an internal pressure of about 9 bar via a nozzle to effect initial dispersing. At a residence time of the nitration mixture (having a spent acid/product phase ratio of 11.7 based on weight and of 9.6 based on volume) in the reactor of 80 s, the flow velocity of the nitration mixture is 0.42 m/s. The temperature in the reactor after the fifth mixing element after initial dispersing is 98° C. and at the end of the reactor is 121° C. The residue content of nitric acid in the spent nitrating acid is 1200 ppm (corresponding to a conversion of nitric acid of 97%). The temperature rise in the nitration mixture is 41° C. The crude nitrobenzene contains, apart from the excess of introduced benzene, less than 120 ppm of dinitrobenzene (DNB) and less than 1200 ppm of nitrophenols with a very small proportion of picrin acid.

Example 2 (According to the Invention)

A mixture of 762 g/h of benzene (10% excess) and 190.5 g/h of recirculated nitrobenzene originating from the nitration (corresponding to 25% of the benzene metered in) and also 15.4 kg/h of mixed acid having a content of sulfuric acid of 65.73% and of nitric acid of 4.99% is metered for an initial temperature of 80° C. into a tube reactor as described in example 1. The benzene/nitrobenzene mixture is introduced into the reactor at an internal pressure of about 9 bar via a nozzle to effect initial dispersing. At a residence time of the nitration mixture (having a spent acid/product phase ratio of 10.2 based on weight and of 8.0 based on volume) in the reactor of 78 s, the flow velocity of the nitration mixture is 0.43 m/s. The temperature in the reactor after the fifth mixing element after initial dispersing is 102° C. and at the end of the reactor is 122.1° C. The residue content of nitric acid in the spent nitrating acid is less than 200 ppm (corresponding to a conversion of nitric acid of 99.5%). The temperature rise in the nitration mixture is 42.1° C. The crude nitrobenzene contains, apart from the excess of introduced benzene, about 80 ppm of dinitrobenzene (DNB) and less than 900 ppm of nitrophenols with a very small proportion of picrin acid.

Example 3 (According to the Invention)

A mixture of 15.4 kg/h of mixed acid having a content of sulfuric acid of 65.73% and of nitric acid of 4.99% and also 190.5 g/h of recirculated nitrobenzene originating from the nitration (corresponding to 1.31% of the mixed acid) and 762 g/h of benzene (10% excess) is metered for an initial temperature of about 80° C. into a tube reactor as described in example 1, with the nitrobenzene being predispersed in the mixed acid before addition of the benzene. The benzene is introduced at an internal pressure of about 9 bar via a nozzle into the mixture of mixed acid and nitrobenzene in the reactor to effect initial dispersing. At a residence time of the nitration mixture having a spent acid/product phase ratio of 10.2 based on weight and of 8.0 based on volume in the reactor of 78 s, the flow velocity of the nitration mixture is 0.43 m/s. The temperature in the reactor after the fifth mixing element after initial predispersing is 102° C. and at the end of the reactor is 122.1° C. The residue content of nitric acid in the spent nitrating acid is less than 200 ppm (corresponding to a conversion of nitric acid of 99.5%). The temperature rise in the nitration mixture is 42.1° C. The crude nitrobenzene contains, apart from the excess of introduced benzene, from about 80 to 90 ppm of dinitrobenzene (DNB) and less than 900 ppm of nitrophenols with a very small proportion of picrin acid.

Example 4 (According to the Invention)

A mixture of 15.4 kg/h of mixed acid having a content of sulfuric acid of 65.73% and of nitric acid of 4.99% and 160 g/h of nitrobenzene (corresponding to 1.1% of the recycle acid) and also a mixture of 762 g/h of benzene (10% excess) and 76 g/h of nitrobenzene (corresponding to 10% of the benzene introduced) is metered for an initial temperature of about 80° C. into a tube reactor as described in example 1, with the nitrobenzene being predispersed in the mixed acid before addition of the benzene. The benzene/nitrobenzene mixture is introduced at an internal pressure of about 9 bar via a nozzle into the mixture of mixed acid and nitrobenzene in the reactor to effect initial dispersing. At a residence time of the nitration mixture having a spent acid/product phase ratio of 10.2 based on weight and of 8.0 based on volume in the reactor of 78 s, the flow velocity of the nitration mixture is about 0.43 m/s. The temperature in the reactor after the fifth mixing element after initial predispersing is 102° C. and at the end of the reactor is 122.1° C. The residue content of nitric acid in the spent nitrating acid is less than 200 ppm (corresponding to a conversion of nitric acid of 99.5%). The temperature rise in the nitration mixture is 42.1° C. The crude nitrobenzene contains, apart from the excess of introduced benzene, about 80 ppm of dinitrobenzene (DNB) and less than 900 ppm of nitrophenols with a very small proportion of picrin acid.

The invention claimed is:

1. A process for the adiabatic nitration of nitratable aromatic organic compounds for producing the corresponding nitrated aromatic organic compounds,
wherein the nitratable aromatic organic compounds are converted, via a nitration reaction in the presence of a nitrating acid mixture comprising nitric acid and sulfuric acid, into the corresponding nitrated aromatic organic compounds,
wherein the spent nitrating acid mixture resulting after the nitration reaction is recycled and circulated to the nitration reaction after the crude nitration aromatic organic compounds have been separated off and after subsequent concentration thereof;
wherein the corresponding nitrated aromatic organic compounds are added to a reaction starting mixture, which reaction starting mixture comprises (i) the nitratable aromatic organic compounds to be nitrated and (ii) a nitrating acid mixture comprising nitric acid and sulfuric acid, and wherein the nitration reaction is started and carried out in the presence of the corresponding nitrated aromatic organic compounds; and
wherein the nitrated aromatic organic compounds obtained are partly recirculated to the nitration reaction and the subsequent nitration reaction is started and carried out in the presence of said nitrated aromatic organic compounds;
wherein the amount of corresponding nitrated aromatic organic compounds added to the nitration reaction is selected in such a way that the amount of added nitrated aromatic organic compounds effects lowering of the interfacial tension between organic phase and acid phase and effects an improved dispersibility of organic phase and acid phase, wherein the amount of nitrated aromatic organic compounds added to the nitration reaction is selected in such a way that the proportion by weight of added aromatic organic compounds, based on the sulfuric acid of the nitrating acid mixture comprising nitric acid and sulfuric acid, is in the range of from 0.02 to 10% by weight, and
wherein the nitrated organic aromatic compounds added to the nitration reaction originate from the nitrated aromatic organic compounds obtained in the vapor condensate after concentration of the spent nitrating acid mixture;
wherein the nitration reaction is carried out under adiabatic reaction conditions, and
wherein the nitration reaction is carried out in a tube reactor.

2. The process as claimed in claim 1,
wherein the spent nitrating acid mixture resulting after the nitration reaction is recycled and circulated to the nitration reaction after the crude nitrated aromatic organic compounds have been separated off.

3. The process as claimed in claim 1,
wherein the amount of nitrated aromatic organic compounds added to the nitration reaction is selected in such a way that the proportion by weight of added nitrated aromatic organic compounds, based on the nitratable aromatic organic compounds to be nitrated, is in the range from 0.01 to 60% by weight.

4. The process as claimed in claim 1,
wherein the nitrated aromatic organic compounds added to the nitration reaction are introduced to at least one of the following positions (i) to (iv):
(i) the reaction starting mixture,
(ii) the sulfuric acid of the nitrating acid mixture comprising nitric acid and sulfuric acid,
(iii) the nitrating acid mixture comprising nitric acid and sulfuric acid,
(iv) the nitratable aromatic organic compounds to be nitrated.

5. The process as claimed in claim 1,
wherein the nitrated aromatic organic compounds added to the nitration reaction are introduced to at least one of the following positions (i) to (iv):
(i) the reaction starting mixture,
(ii) the sulfuric acid of the nitrating acid mixture comprising nitric acid and sulfuric acid before production of the nitrating acid mixture,
(in) the nitrating acid mixture comprising nitric acid and sulfuric acid,
(iv) the nitratable aromatic organic compounds to be nitrated.

6. The process as claimed in claim 1,
wherein the nitrated aromatic organic compounds added to the nitration reaction are introduced into both the organic phase and also the acid phase of the reaction starting mixture.

7. The process as claimed in claim 1,
wherein the nitrated aromatic organic compounds added to the nitration reaction are introduced into both the organic phase and also the acid phase of the reaction starting mixture, wherein from 0.1 to 35% by weight, based on the organic phase, of nitrated aromatic organic compounds are added to the organic phase and wherein from 0.01 to 3% by weight, based on the acid phase, of nitrated aromatic organic compounds are added to the acid phase.

8. The process as claimed in claim 1,
wherein the spent nitrating acid mixture resulting after the nitration reaction is, after the crude nitrated aromatic organic compounds have been separated off and after subsequent concentration and optional addition of at least one of fresh nitric acid and fresh sulfuric acid, recycled and recirculated to the nitration reaction.

9. The process as claimed in claim 1,
wherein the spent nitrating acid mixture resulting after the nitration reaction is, after the crude nitrated aromatic organic compounds have been separated off and after subsequent concentration and optional addition of at least one of fresh nitric acid and fresh sulfuric acid, recycled and recirculated to the nitration reaction, wherein the nitrated aromatic organic compounds added for the nitration reaction are introduced into the spent nitrating acid mixture which has been concentrated and optionally admixed with at least one of fresh nitric acid, sulfuric acid and nitratable aromatic organic compounds to be nitrated.

10. The process as claimed in claim 1,
wherein the spent nitrating acid mixture resulting after the nitration reaction is, after the crude nitrated aromatic organic compounds have been separated off and after subsequent concentration and optional addition of at least one of fresh nitric acid and fresh sulfuric acid, recycled and recirculated to the nitration reaction, wherein the nitrated aromatic organic compounds added for the nitration reaction are introduced into the spent nitrating acid mixture which has been concentrated and optionally admixed with at least one of fresh nitric acid, sulfuric acid and nitratable aromatic organic compounds to be nitrated, wherein the nitratable aromatic organic compounds are introduced immediately before commencement of reaction or as last, on a time basis, reaction component.

11. The process as claimed in claim 1,
wherein the spent nitrating acid mixture resulting after the nitration reaction is, after the crude nitrated aromatic organic compounds have been separated off and after subsequent concentration and optional addition of at least one of fresh nitric acid and fresh sulfuric acid, recycled and recirculated to the nitration reaction, wherein the nitrated aromatic organic compounds added for the nitration reaction are introduced into the spent nitrating acid mixture which has been concentrated and optionally admixed with at least one of fresh nitric acid, sulfuric acid and nitratable aromatic organic compounds to be nitrated, wherein the nitratable aromatic organic compounds are introduced immediately before commencement of reaction or as last, on a time basis, reaction component before the first dispersing operation initiating the nitration reaction.

12. The process as claimed in claim 1,
wherein the spent nitrating acid mixture resulting after the nitration reaction is, after the crude nitrated aromatic organic compounds have been separated off and after subsequent concentration and optional addition of at least one of fresh nitric acid and fresh sulfuric acid, recycled and recirculated to the nitration reaction, wherein a dispersion of concentrated recycled acid, nitratable aromatic organic compounds to be nitrated and nitrated aromatic organic compounds is firstly produced, wherein nitric acid is subsequently added to the dispersion and the nitration reaction is initiated in this way.

13. A method for at least one of lowering the interfacial tension of an organic phase and an add phase and improving the dispersibility of an organic phase and an add phase in nitration reactions of nitratable aromatic organic compounds by the use of nitrated aromatic organic compounds,
wherein the nitratable aromatic organic compounds are converted, via an adiabatic nitration reaction in the presence of a nitrating acid mixture comprising nitric acid and sulfuric acid, into the corresponding nitrated aromatic organic compounds;
wherein the spent nitrating acid mixture resulting after the nitration reaction is recycled and circulated to the nitration reaction after the crude nitration aromatic organic compounds have been separated off and after subsequent concentration thereof;
wherein the corresponding nitrated aromatic organic compounds are added to a reaction starting mixture, which reaction starting mixture comprises (i) the nitratable aromatic organic compounds to be nitrated and (ii) a nitrating acid mixture comprising nitric acid and sulfuric acid, and wherein the nitration reaction is started and carried out in the presence of the corresponding nitrated aromatic organic compounds; and
wherein the nitrated aromatic organic compounds obtained are partly recirculated to the nitration reaction and the subsequent nitration reaction is started and carried out in the presence of said nitrated aromatic organic compounds;
wherein the amount of corresponding nitrated aromatic organic compounds added to the nitration reaction is selected in such a way that the amount of added nitrated aromatic organic compounds effects lowering of the interfacial tension between organic phase and acid phase and effects an improved dispersibility of organic phase and acid phase, wherein the amount of nitrated aromatic organic compounds added to the nitration reaction is selected in such a way that the proportion by weight of added aromatic organic compounds, based on the sulfuric acid of the nitrating acid mixture comprising nitric acid and sulfuric acid, is in the range of from 0.02 to 10% by weight, and
wherein the nitrated organic aromatic compounds added to the nitration reaction originate from the nitrated aromatic organic compounds obtained in the vapor condensate after concentration of the spent nitrating acid mixture;
wherein the nitration reaction is carried out under adiabatic reaction conditions, and
wherein the nitration reaction is carried out in a tube reactor.

14. A method for at least one of increasing the yields and reducing by-product formation and shortening the total reaction times and lowering the reaction start temperatures in nitration reactions of nitratable aromatic organic compounds by the use of nitrated aromatic organic compounds,
- wherein the nitratable aromatic organic compounds are converted, via an adiabatic nitration reaction in the presence of a nitrating acid mixture comprising nitric acid and sulfuric acid, into the corresponding nitrated aromatic organic compounds;
- wherein the spent nitrating acid mixture resulting after the nitration reaction is recycled and circulated to the nitration reaction after the crude nitration aromatic organic compounds have been separated off and after subsequent concentration thereof;
- wherein the corresponding nitrated aromatic organic compounds are added to a reaction starting mixture, which reaction starting mixture comprises (i) the nitratable aromatic organic compounds to be nitrated and (ii) a nitrating acid mixture comprising nitric add and sulfuric add, and wherein the nitration reaction is started and carried out in the presence of the corresponding nitrated aromatic organic compounds; and
- wherein the nitrated aromatic organic compounds obtained are partly recirculated to the nitration reaction and the subsequent nitration reaction is started and carried out in the presence of said nitrated aromatic organic compounds;
- wherein the amount of corresponding nitrated aromatic organic compounds added to the nitration reaction is selected in such a way that the amount of added nitrated aromatic organic compounds effects lowering of the interfacial tension between organic phase and acid phase and effects an improved dispersibility of organic phase and acid phase, wherein the amount of nitrated aromatic organic compounds added to the nitration reaction is selected in such a way that the proportion by weight of added aromatic organic compounds, based on the sulfuric acid of the nitrating acid mixture comprising nitric acid and sulfuric acid, is in the range of from 0.02 to 10% by weight, and
- wherein the nitrated organic aromatic compounds added to the nitration reaction originate from the nitrated aromatic organic compounds obtained in the vapor condensate after concentration of the spent nitrating acid mixture;
- wherein the nitration reaction is carried out under adiabatic reaction conditions, and
- wherein the nitration reaction is carried out in a tube reactor.

* * * * *